US012295781B2

(12) United States Patent
Ta

(10) Patent No.: US 12,295,781 B2
(45) Date of Patent: May 13, 2025

(54) SYSTEMS, METHODS, AND DEVICES DIRECTED TO ULTRASONIC NEEDLE POSITIONING APPARATUS

(71) Applicant: Ultrasertion Corporation, Anaheim, CA (US)

(72) Inventor: Liem Phuc Quang Ta, Anaheim Hills, CA (US)

( * ) Notice: Subject to any disclaimer, the term of this patent is extended or adjusted under 35 U.S.C. 154(b) by 0 days.

(21) Appl. No.: 17/810,555

(22) Filed: Jul. 1, 2022

(65) Prior Publication Data

US 2023/0000462 A1 Jan. 5, 2023

Related U.S. Application Data

(60) Provisional application No. 63/218,191, filed on Jul. 2, 2021.

(51) Int. Cl.
*A61B 8/08* (2006.01)
*A61B 17/34* (2006.01)

(52) U.S. Cl.
CPC ........ *A61B 8/0841* (2013.01); *A61B 17/3403* (2013.01); *A61B 2017/3413* (2013.01)

(58) Field of Classification Search
CPC ........ A61B 17/3403; A61B 2017/3407; A61B 2017/3413; A61B 8/0841; A61B 8/085; A61B 8/4411; A61B 8/4422; A61B 8/46
See application file for complete search history.

(56) References Cited

U.S. PATENT DOCUMENTS

| 5,671,747 A | * | 9/1997 | Connor | A61B 8/4455 600/459 |
| 2009/0082782 A1 | * | 3/2009 | Kalpin | A61B 90/98 606/130 |
| 2015/0272700 A1 | * | 10/2015 | Masuda | A61B 5/061 600/424 |
| 2018/0235649 A1 | * | 8/2018 | Elkadi | A61B 18/1445 |
| 2021/0045711 A1 | * | 2/2021 | Brattain | A61B 8/0891 |
| 2021/0161612 A1 | * | 6/2021 | Black | A61B 34/20 |
| 2021/0186450 A1 | * | 6/2021 | Vancamberg | A61B 6/584 |

FOREIGN PATENT DOCUMENTS

| CN | 112168299 A | * | 1/2021 | ......... A61B 17/3403 |
| JP | 2003334191 A | * | 11/2003 | |

* cited by examiner

*Primary Examiner* — Joseph M Santos Rodriguez
*Assistant Examiner* — Maria Christina Talty
(74) *Attorney, Agent, or Firm* — Knobbe Martens Olson & Bear LLP

(57) ABSTRACT

In some embodiments, an apparatus and methods for inserting a needle into a patient is disclosed. An apparatus can include a base having a cavity for receiving an ultrasound probe, a swing arm, a first linear position sensing track, a second linear position sensing track, an angle sensor disposed about a pivot point, a needle holder configured to move along the first linear position sensing track, and an insertion depth slider configured to move along the second linear position sensing track.

22 Claims, 41 Drawing Sheets

SYSTEMS, METHODS, AND DEVICES DIRECTED TO ULTRASONIC NEEDLE POSITIONING APPARATUS

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

This application claims priority to U.S. Provisional Patent Application No. 63/218,191, entitled "SYSTEMS, METHODS, AND DEVICES DIRECTED TO ULTRASONIC NEEDLE POSITIONING APPARATUS," filed Jul. 2, 2021, the entire contents of which are hereby incorporated by reference herein in its entirety and for all purposes.

BACKGROUND

Field

The embodiments of the disclosure generally relate to ultrasound-guided systems, and more particularly to systems, devices, and methods for ultrasound-guided needle positioning technology for use in medical procedures.

Description

The approaches described in this section are approaches that could be pursued, but not necessarily approaches that have been previously conceived or pursued. Therefore, unless otherwise indicated, it should not be assumed that any of the approaches described in this section qualify as prior art merely by virtue of their inclusion in this section.

Inserting catheters and other medical devices into patients can be important, but often difficulties can arise when a patient is uncooperative or when it is difficult to locate a vein, for example to due to drug use or obesity, which can lead to wasted time and frustration on the part of medical providers and patients.

SUMMARY OF THE INVENTION

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

The systems, methods, and devices described herein each have several aspects, no single one of which is solely responsible for its desirable attributes. Without limiting the scope of this disclosure, several non-limiting features will now be described briefly.

In some aspects, the techniques described herein relate to an apparatus for accessing a lumen of a patient, the apparatus including: a base, the base having a cavity for receiving an ultrasound probe; a swing arm pivotably coupled to the base at a pivot point, the pivot point located at a distal end of the swing arm; a first linear position sensing track; a second linear position sensing track; an angle sensor disposed about the pivot point; a needle holder configured to move along the first linear position sensing track; an insertion depth slider configured to move along the second linear position sensing track; a power source; a computer readable storage medium having program instructions embodied therewith; and one or more processors configured to execute the program instructions to cause the apparatus to: prompt a user to measure a length of a needle; determine, using the first linear position sensing track and the needle holder, the length of the needle; prompt the user to set an insertion depth for the needle; determine, using the second linear position sensing track and the insertion depth slider, the insertion depth of the needle; determine, using the angle sensor, an insertion angle, wherein the insertion angle is an angle of the swing arm with respect to the base; prompt the user to insert the needle into the lumen; based at least in part on the needle length and the insertion angle, determine that the user has inserted the needle to the insertion depth; and provide an indication to the user that the needle has been inserted to the insertion depth.

In some aspects, the techniques described herein relate to an apparatus, wherein a bottom surface of the base is curved.

In some aspects, the techniques described herein relate to an apparatus, wherein a bottom surface of the base is flat.

In some aspects, the techniques described herein relate to an apparatus, wherein the computer-readable storage medium further includes instructions that, when executed by the one or more processors, cause the apparatus to: compare the angle of the swing arm to a target angle; and provide an indication to the user when the angle of the swing arm is within a threshold angle of the target angle.

In some aspects, the techniques described herein relate to an apparatus, wherein the threshold angle is about 1 degree.

In some aspects, the techniques described herein relate to an apparatus, further including a display.

In some aspects, the techniques described herein relate to an apparatus, wherein the computer-readable storage medium further includes instructions that, when executed by the one or more processors, cause the apparatus to: after prompting the user to set the needle length, display a current needle length; after prompting the user to set the insertion depth, display a current insertion depth; and after prompting the user to set the insertion angle, display a current insertion angle, wherein the current needle length changes as the user moves the needle slider along the first linear position sensing track, wherein the current insertion depth changes as the user moves the insertion depth slider along the second linear position sensing track, and wherein the current insertion angle changes as the user adjusts the angle of the swing arm.

In some aspects, the techniques described herein relate to an apparatus, further including at least one guide bar, wherein the at least one guide bar is positioned in a sensing path of the ultrasound probe.

In some aspects, the techniques described herein relate to an apparatus, wherein the indication includes any combination of one or more of illuminating an LED, altering content of a display, and playing a sound.

In some aspects, the techniques described herein relate to an apparatus, further including: a needle measurement hole disposed at a proximal end of the swing arm; and a hilt sensor located at the needle measurement hole and configured to be activated by a hilt of the needle, wherein determining the length of the needle includes determining that the hilt sensor has been activated.

In some aspects, the techniques described herein relate to an apparatus, wherein the computer-readable storage medium further includes instructions that, when executed by the one or more processors, cause the apparatus to: determine if the needle length is within an allowed range; and if the needle is within the allowed range, display an indication that the needle length is within the allowed range; if the needle is not within the allowed range, display an indication that the needle length is not within the allowed range.

In some aspects, the techniques described herein relate to a method for accessing a lumen of a patient, the method including: prompting a user to measure a length of a needle; determining, using a first linear position sensing track and a needle holder, the length of the needle; prompting the user to set an insertion depth for the needle; determining, using a second linear position sensing track and an insertion depth slider, the insertion depth of the needle; determining, using an angle sensor, an insertion angle, wherein the insertion angle is an angle of a swing arm with respect to the base; prompting the user to insert the needle into the lumen; based at least in part on the needle length and the insertion angle, determining that the user has inserted the needle to the insertion depth; and providing an indication to the user that the needle has been inserted to the insertion depth.

In some aspects, the techniques described herein relate to a method, further including: comparing the angle of the swing arm to a target angle; and providing an indication to the user when the angle of the swing arm is within a threshold angle of the target angle.

In some aspects, the techniques described herein relate to a method, wherein the threshold angle is about 1 degree.

In some aspects, the techniques described herein relate to a method, further including: after prompting the user to set the needle length, displaying a current needle length on a display; after prompting the user to set the insertion depth, displaying a current insertion depth on the display; and after prompting the user to set the insertion angle, displaying a current insertion angle on the display, wherein the current needle length changes as the user moves the needle slider along the first linear position sensing track, wherein the current insertion depth changes as the user moves the insertion depth slider along the second linear position sensing track, and wherein the current insertion angle changes as the user adjusts the angle of the swing arm.

In some aspects, the techniques described herein relate to a method, wherein the indication includes any combination of one or more of illuminating an LED, altering content of a display, and playing a sound.

In some aspects, the techniques described herein relate to a method, wherein determining the length of the needle includes determining that a hilt sensor has been activated.

In some aspects, the techniques described herein relate to a method, further including: determining if the needle length is within an allowed range; and if the needle length is within the allowed range, displaying an indication that the needle length is within the allowed range; if the needle is not within the allowed range, displaying an indication that the needle length is not within the allowed range.

In some aspects, the techniques described herein relate to a method, wherein the allowed range is 2 cm or more.

In some aspects, the techniques described herein relate to a method, further including: determining if the needle insertion depth length is within an allowed range; and if the needle insertion depth is within the allowed range, displaying an indication that the needle insertion depth is within the allowed range; if the needle insertion depth is not within the allowed range, displaying an indication that the needle insertion depth is not within the allowed range.

BRIEF DESCRIPTION OF THE DRAWINGS

These and other features, aspects, and advantages of the present application are described with reference to drawings off certain embodiments, which are intended to illustrate, but not limit, the present disclosure. It is to be understood that the attached drawings are for the purpose of illustrating concepts disclosed in the present application and may not be to scale.

DETAILED DESCRIPTION

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Figure 1:
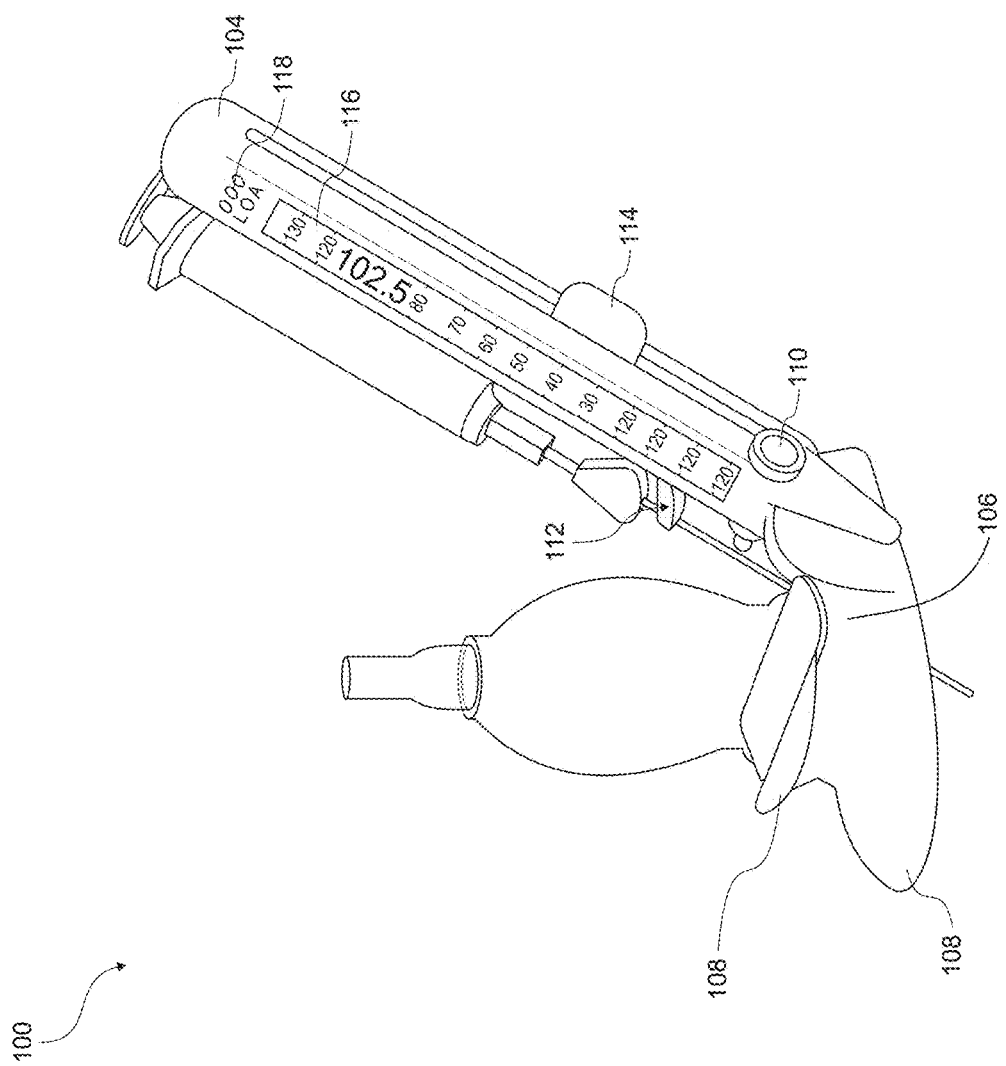
FIG. 1 is a view of an example embodiment of an insertion apparatus.

In some embodiments, the systems disclosed herein comprise an apparatus that holds an ultrasound probe and a needle in a particular alignment with respect to one another, for example as illustrated in FIG. 1. The apparatus 100 has a base 102, a swing arm 104 for angling and supporting a needle, cavity 106 for receiving an ultrasound probe, and finger hole 108 for receiving a finger of the user. The apparatus can be used to set and control a needle trajectory to increase the likelihood that the needle hits its target (e.g., a lumen in a patient, such as a vein) and does not hit other structures in the body. Some embodiments disclosed herein can make it easier to perform accurate needle insertions and procedures on "hard stick" patients (patients for whom drawing blood or placing a line is difficult due to obesity, drug abuse, or other factors). Some embodiments herein can simplify procedures by providing assistive devices that can be used to reliably insert a needle to an identified target location in the patient's body. The embodiments herein can be used for a variety of procedures including, for example, thoracentesis, paracentesis, central line placement, arterial line placement, nerve block, tumor biopsy, and so forth. In some embodiments, the systems, methods, and devices disclosed herein can be used by physicians, nurses, veterinarians, and other medical personnel. In some embodiments, a device can be powered and can have one or more active components to assist the user. In some embodiments, an apparatus can be unpowered. For example, an apparatus can use mechanically coupled components and passive indicators.

Figure 2:
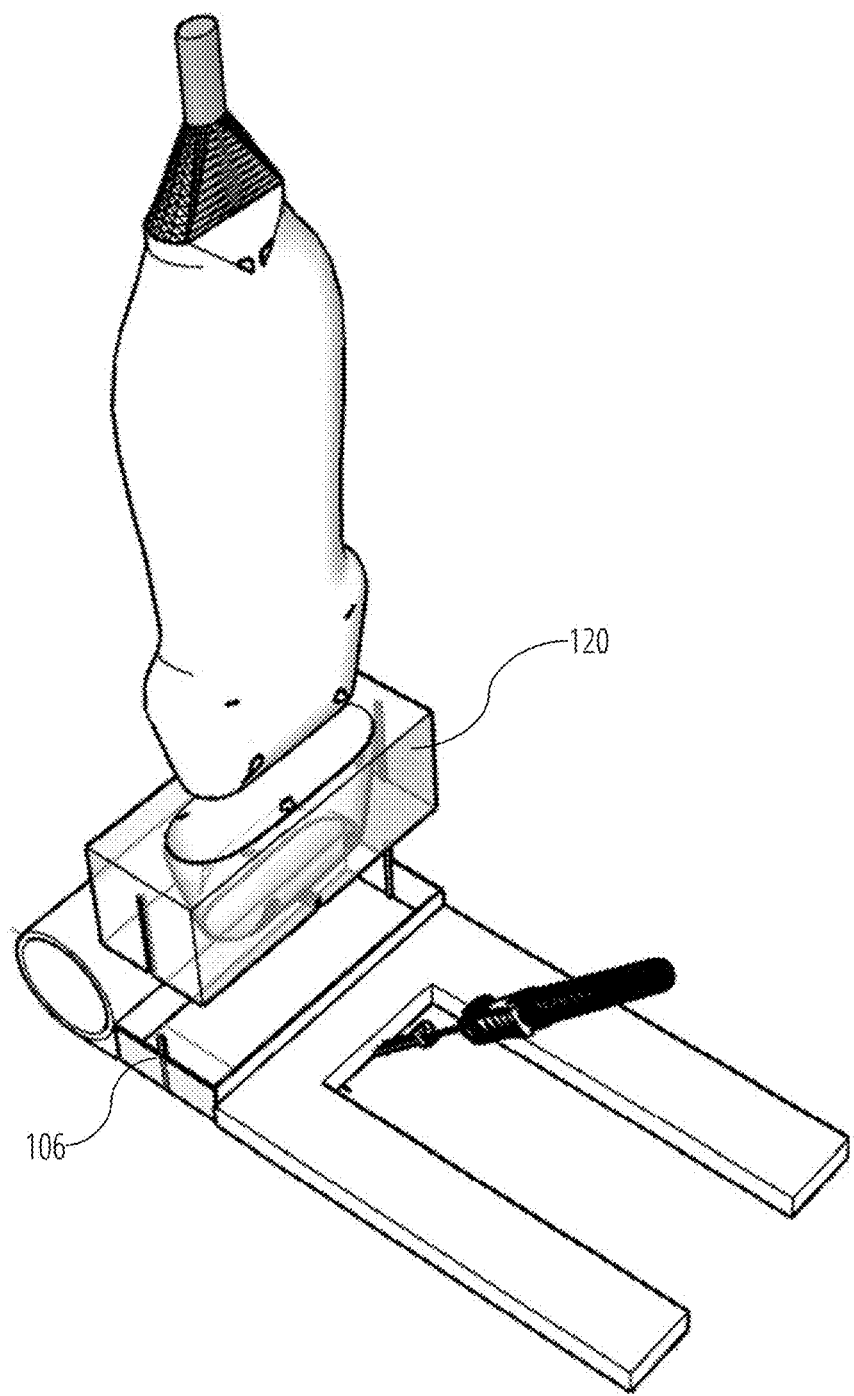
FIG. 2 is a view of an example embodiment of a modular cavity insert and a base having a cavity formed for received said insert.

In some embodiments, a device comprises a cavity for receiving an ultrasound probe. In some embodiments, as shown in FIG. 2, a modular cavity insert 120 can be used for holding different ultrasound probes inside a standardized cavity 106, while in other embodiments, apparatuses can be manufactured to fit a specific ultrasound probe. A modular cavity insert 120 can have several advantages. For example, an apparatus can include cavity inserts to accommodate different ultrasound probes. In some cases, a hospital or other user of the apparatus can keep a stock of apparatuses and a separate stock of inserts. In some cases, a manufacturer can have a single SKU for an apparatus that can accommodate different ultrasound probes, which can simplify supply chain issues. However, such an approach can increase cost and complexity as a result of having a separate modular cavity insert component.

Figure 3:
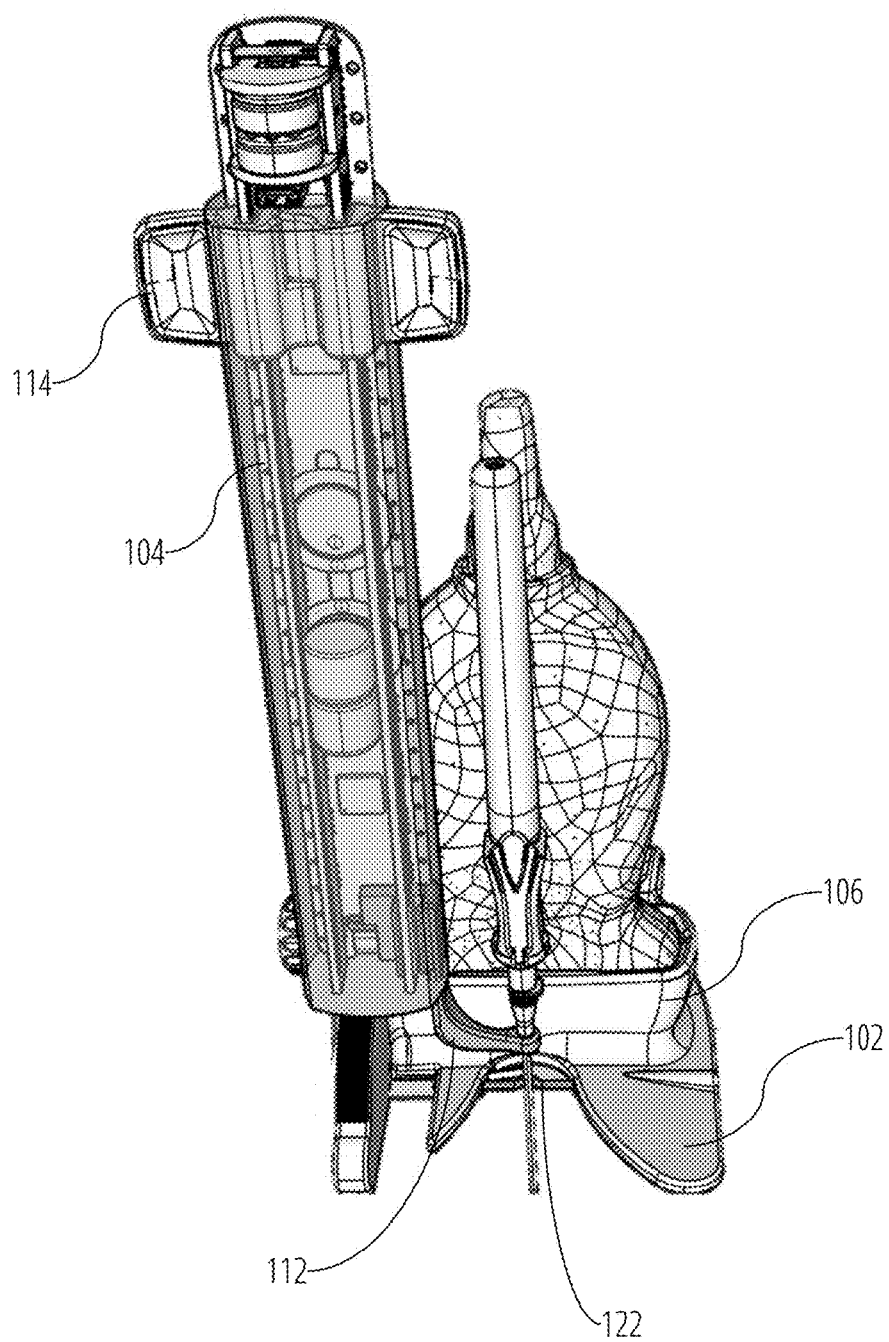
FIG. 3 is a view of an example embodiment of an insertion apparatus.
Figure 4:
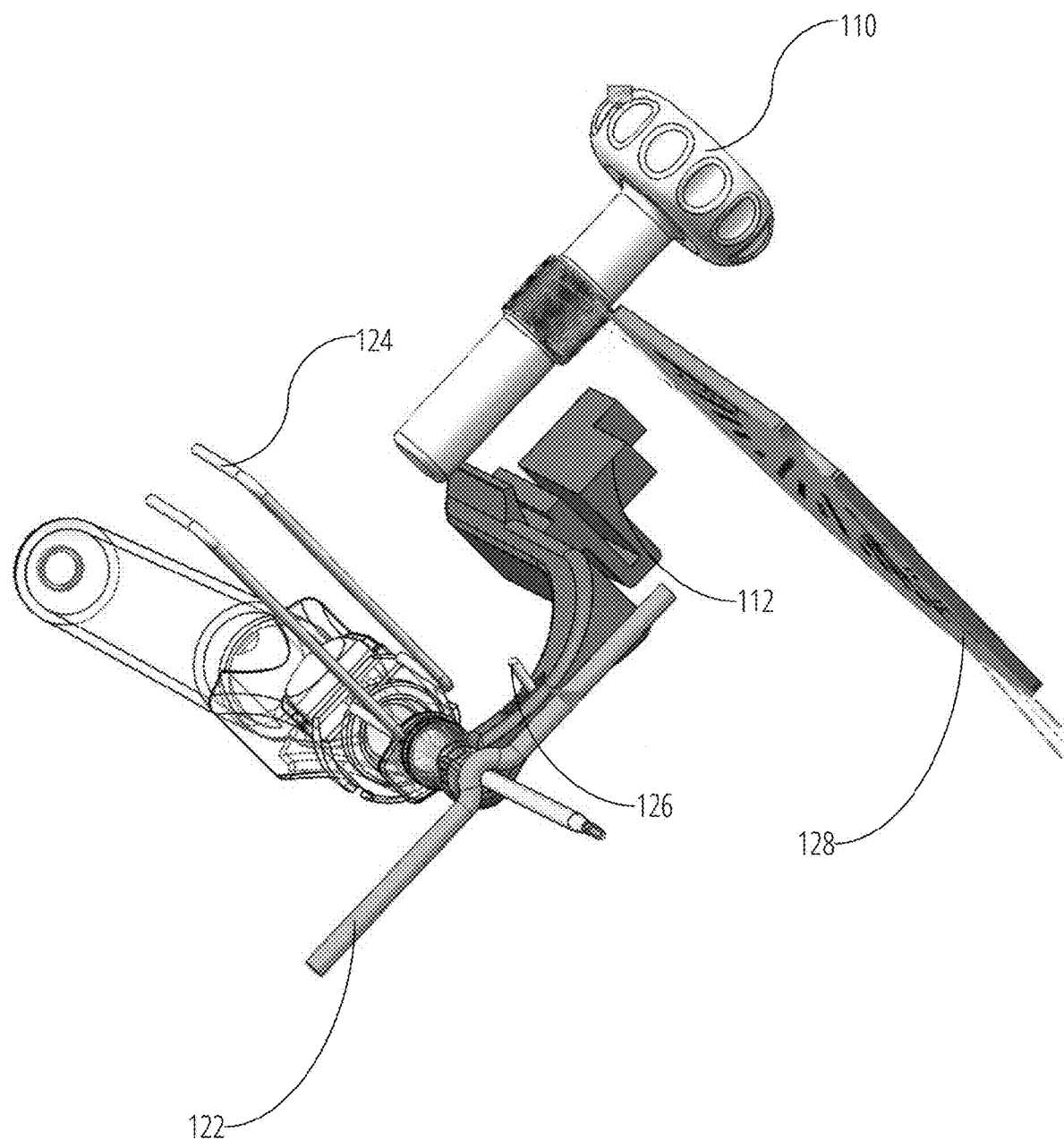
FIG. 4 is a view of example embodiments of components of an insertion apparatus.

In some embodiments, as shown in FIGS. 3 and 4, a device can include a needle support bracket 122 that is placed distally (e.g., near the tip of the needle and near the patient's skin) that can operate to stabilize the needle and thus to aid the user in inserting the needle to the desired location and depth. The needle can pass through a needle guide 112 that is mechanically coupled to the swing arm 104. In some embodiments, the needle guide 112 can be a separate component that is attached to the swing arm 104. In some embodiments, the system can include an angle adjustment knob 110 for setting the angle of the swing arm 104 with respect to the base 102, thereby change the insertion angle of the needle.

In some embodiments, a device can have guide bars 124, as shown in FIG. 4. The guide bars 124 can be positioned such that they pass under an ultrasound probe placed in the cavity 106. The guide bars 124 can disrupt the ultrasound probe, thereby producing a "shadow" on the ultrasound image, which can be used to help position and guide the needle into the desired location. For example, the device can be configured such that the needle will pass between the guide bars 124 when it is inserted into the patient. It will be appreciated that while FIG. 4 illustrates an embodiment with two guide bars 124 with the needle centered between them, some embodiments can include more or fewer guide bars. For example, some embodiments can include one guide bar or can include no guide bars.

For some types of procedures, such as blood draws, the apparatus 100 can remain in place on the patient throughout the procedure. However, for some procedures, such as when inserting a catheter, it can be desirable to remove the apparatus 100 so that a provider can complete the procedure, or to allow the provider to move the needle freely (or partially freely, for example one degree of freedom, two degrees of freedom, three degrees of freedom, etc.) after the needle is inserted into the patient, even if the apparatus 100 is not completely removed. Thus, some embodiments of the apparatus 100 can include a needle release mechanism. For example, a needle guide 112 can have a display 116 that can be released to allow the needle to escape the needle guide 112.

Such a release mechanism can be important for some types of procedures. For example, when inserting a catheter, the needle may initially be inserted at a relatively high angle. However, it can be important to reduce the angle of the needle relative to the patient's skin before inserting the catheter. If the angle is too steep, the catheter could get stuck or break through the vein, for example.

Figure 5A:
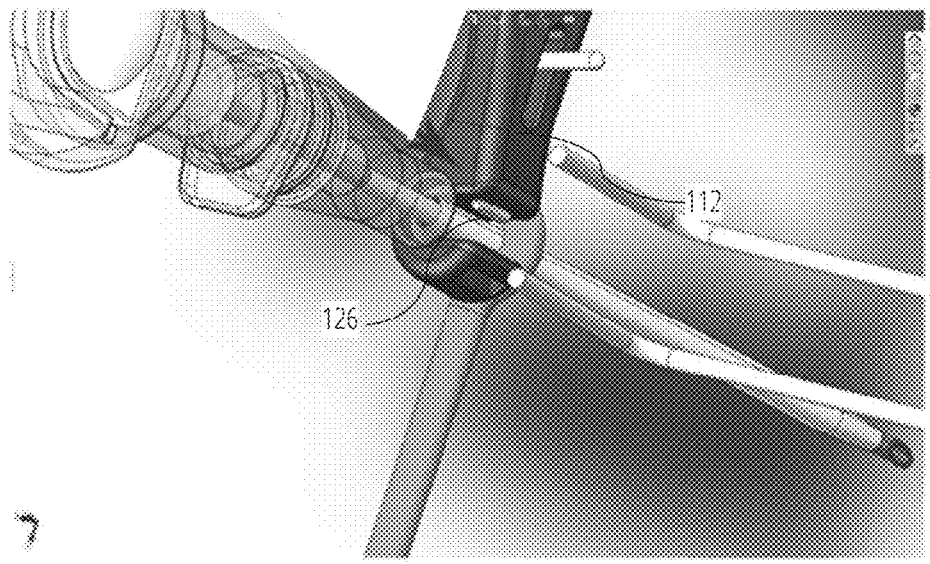
FIGS. 5A-5C show views of example needle release mechanisms according to some embodiments.
Figure 5B:
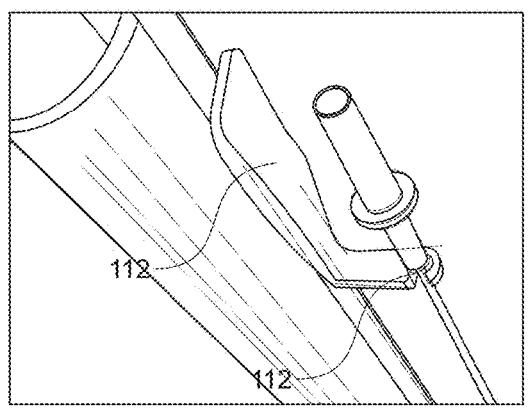
Figure 5C:
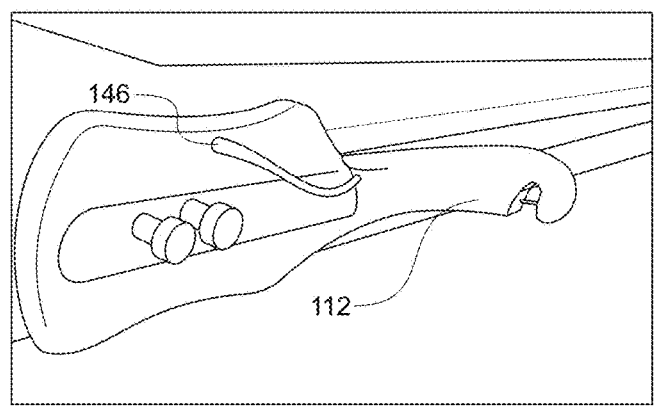

FIGS. 5A-5C illustrate example embodiments of needle guides 112 having needle locks 126. The needle lock 126 can be located at the top, bottom, or side of the needle guide 112. A needle guide 112 can include a needle release trigger 146. The needle release trigger 146 can cause the needle lock 126 to slide out of place, thereby opening the hole in the needle guide 112 and permitting the needle to be removed from the needle guide 112, for example by altering the angle of the needle.

Electronic Positioning

Correct positioning of the needle can be important for ensuring that the needle is inserted to the appropriate location inside the patient's body. Thus, some embodiments of the apparatus 100 can include one or more electronic sensors for measuring and setting needle length, insertion angle, insertion depth, and so forth. The electronic sensors can be linear position sensors, angle sensors, etc.

In some embodiments, the apparatus 100 comprises a central processing unit and a computer-readable storage medium. The apparatus 100 can be configured to determine a trajectory and to guide a user during a needle insertion procedure by determining and setting several values as discussed more fully below.

Figure 6A:
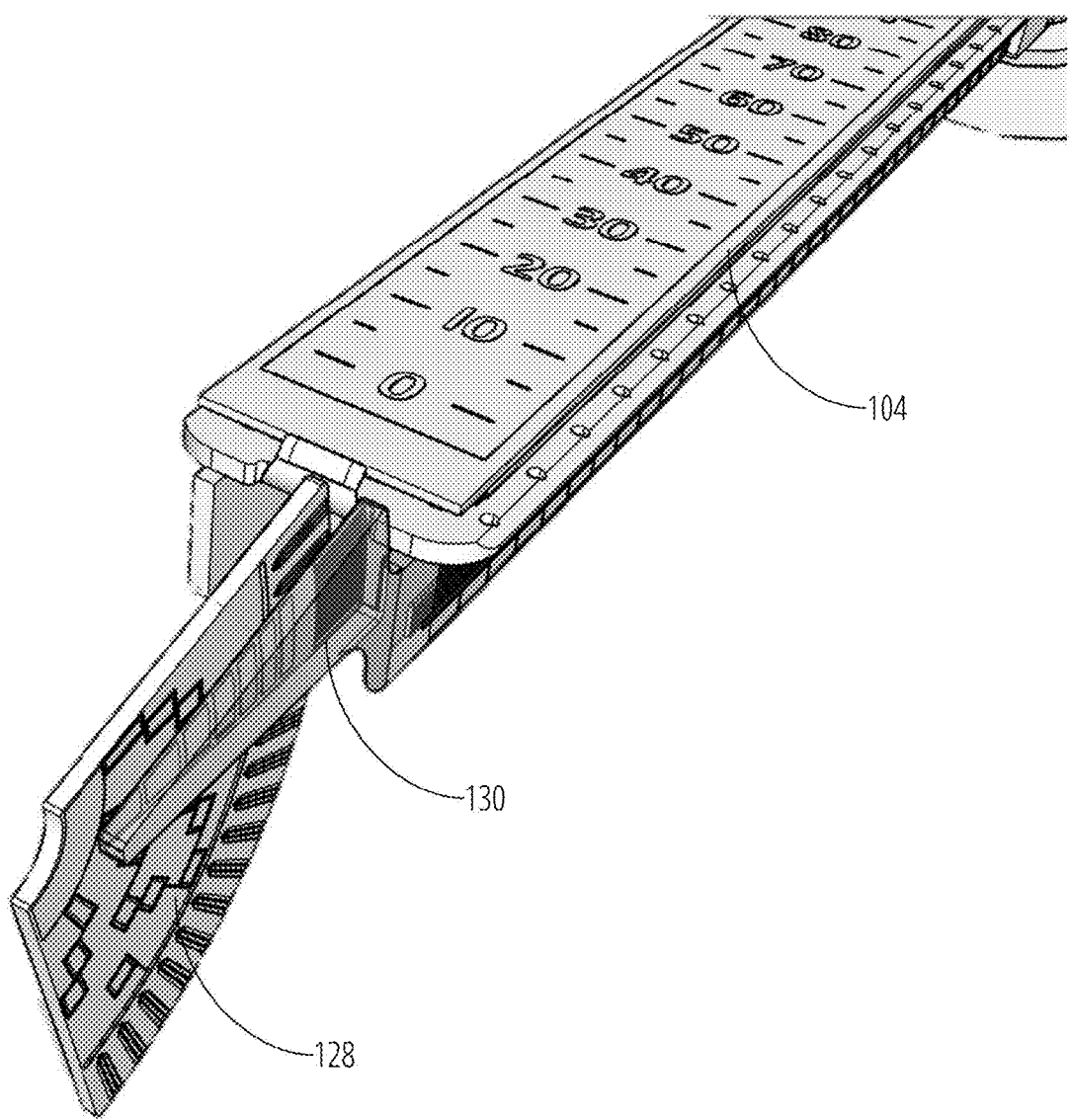
FIG. 6A is a view of an example embodiment of a swing arm and angle position sensor.

As shown in FIG. 6A, in some embodiments, the swing arm 104 can have an active angle sensor arm 130 disposed at or near the distal end of the swing arm 104. A passive angle sensor plate 128 can be mounted to the base 102 of the apparatus 100. The passive angle sensor plate 128 can have a plurality of electrodes disposed thereon that can be used for detecting the angle of the swing arm 104 with respect to the base 102. For example, as the active angle sensor arm 130 passes over the electrically conductive components of the passive angle sensor plate 128, electronics inside the swing arm 104 (as shown in FIG. 6B) can determine the angle of the swing arm 104 by sensing, for example, capacitance, resistance, whether or not circuits are completed, which circuits are completed, and so forth, and particular combinations of measured values can indicate the angle of the swing arm 104 with respect to the base 102.

Figure 6B:
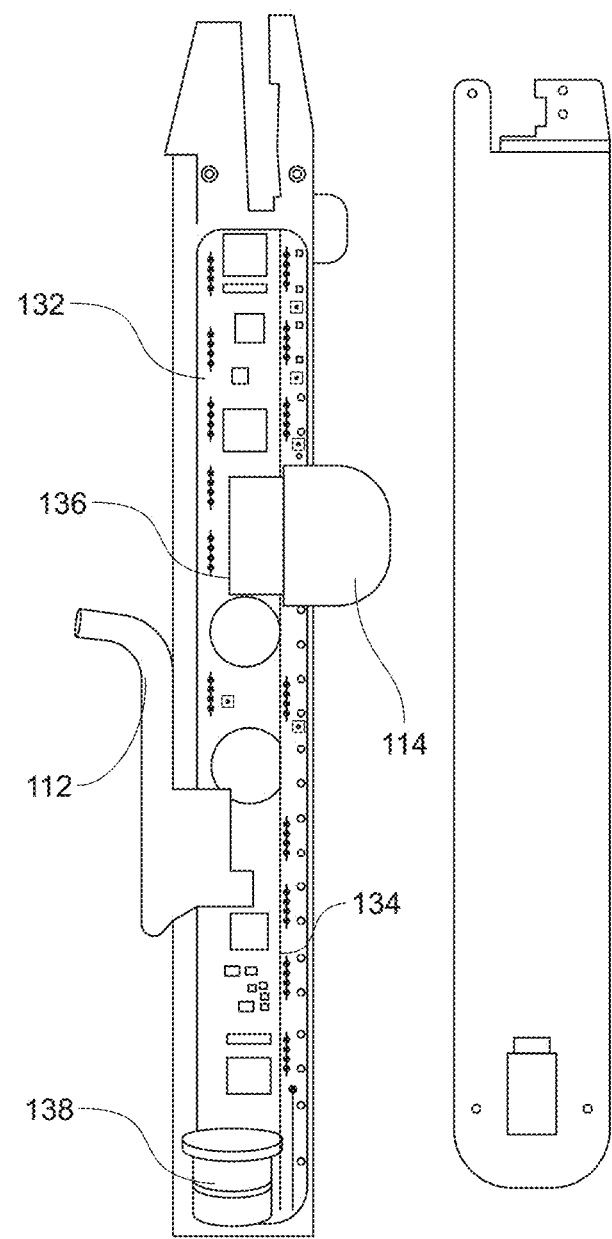
FIG. 6B is a partially disassembled view of a swing arm and related components according to some embodiments.
Figure 6C:
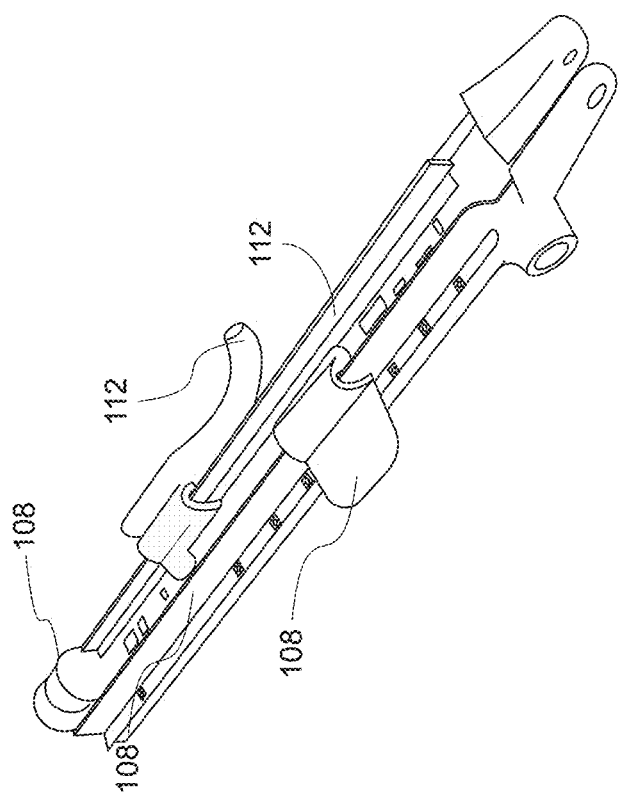
FIG. 6C is a view of some components of a swing arm and needle holder according to some embodiments.

Turning to FIG. 6B, in some embodiments an apparatus 100 can include a swing arm 104. The swing arm 104 can have disposed therein a first track 132 and a second track 134. The first track 132 and second track 134 can be coupled (i.e., mechanically coupled and electrically coupled) to a printed circuit board (PCB), main PCB 136. The main PCB 136 can include components for performing calculations, storing computer-executable instructions, controlling the LED array 118, the display 116, and so forth. The swing arm 104 can have a power source 138 disposed therein. For example, the power source 138 can be a battery or a plurality of batteries. The needle guide 112 can be configured to slide along the first track 132. The insertion depth slider 114 can be configured to slide along the second track 134. As discussed more fully below, the first track 132 and second track 134 can include active sensing components for determining the position of the needle guide 112 and the insertion depth slider 114, respectively. The needle guide 112 and insertion depth slider 114 can include one or more conductive components that can work with the active sensing components of the first track 132 and the second track 134 to determine the position of the needle guide 112 and the insertion depth slider 114. FIG. 6C shows another view of the internal components of a swing arm 104 according to some embodiments.

Figure 6D:
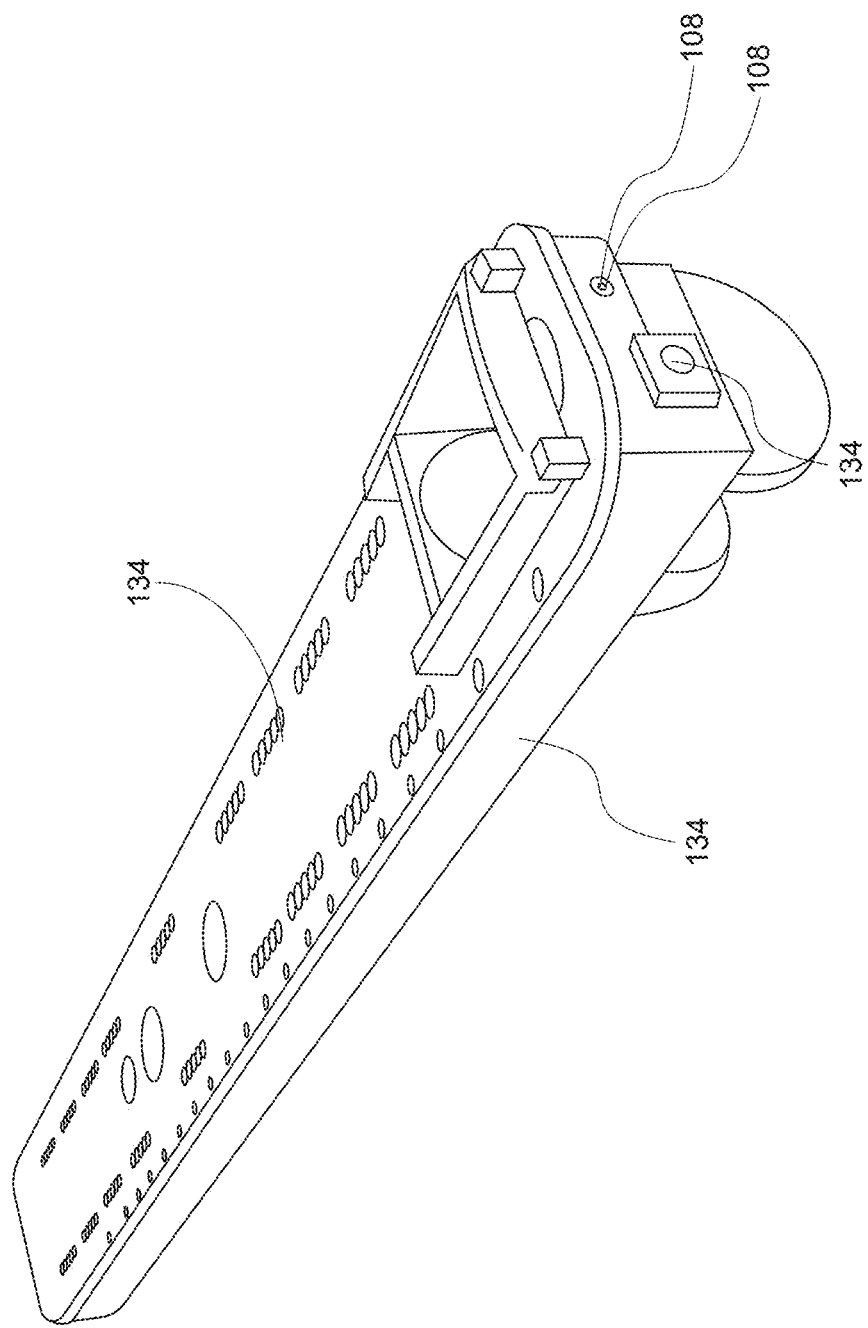
FIG. 6D is a view of some components of a swing arm according to some embodiments.

FIG. 6D shows a main PCB 136 outside the housing of the swing arm 104. As shown in FIG. 6D, the second track 134 can be coupled to the main PCB 136. A needle measurement hole 140 can be disposed at the proximal end of the main PCB 136 (e.g., on a riser board or a section of PCB perpendicular to the main PCB 136 and can correspond to a hole at the proximal end of the swing arm 104. Disposed about the needle measurement hole 140 is a hilt sensor 142. The hilt sensor 142 can be an optical sensor, an electronic sensor, and so forth. The needle measurement hole 140 can be aligned such that when a user inserts a needle through the needle measurement hole 140, the needle pushes the needle guide 112 along the first track 132 inside the swing arm 104. When the hilt (or hub) of the needle hits the hilt sensor 142, the apparatus can determine the length of the needle based on the position of the needle guide 112 along the first track 132.

As discussed above, an apparatus 100 can include various sensors for measuring distances, angles, and so forth. Accordingly, it can be advantageous to provide input and output devices to enable a user to interact with the apparatus 100. The apparatus 100 can include a user input button 144 for interacting with the apparatus 100. For example, the user input button 144 can be used to power on the device, to confirm inputs, to change units (e.g., changing a needle length, insertion depth, etc. from millimeters to centimeters), to alter configuration settings (e.g., minimum and/or maximum allowable deviations from target values), to power off the device, and so forth.

Figure 6E:
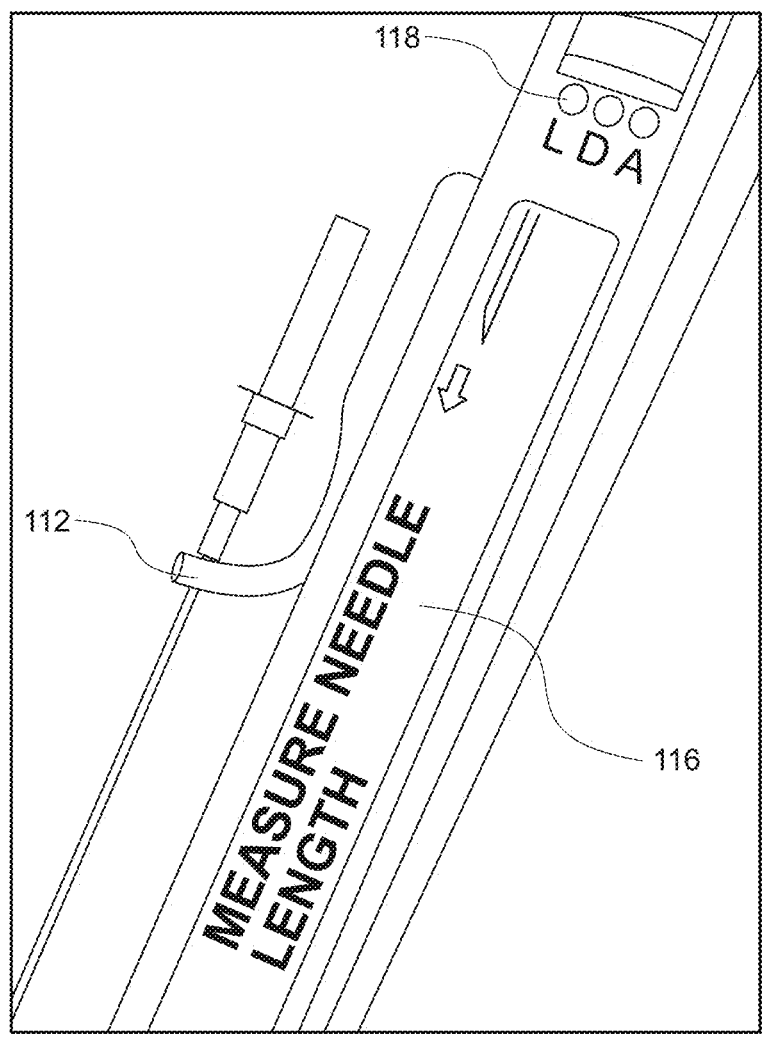
FIG. 6E is a view of some components of a swing arm according to some embodiments.

As shown in FIG. 6E, the apparatus 100 can include a display 116 and LED array 118, which can be disposed on the swing arm 104. The display 116 can provide instructions to the user, provide feedback to the user, and so forth. In some embodiments the LED array 118 can include a plurality of LEDs. The LED array 118 can have LEDs of different colors. For example, the LED array 118 can include red LEDs to indicate an error state and green LEDs to indicate a success state. The number of LEDs in the LED array 118 can vary, for example depending on the adjustments available to the user. In the case where a user can adjust the needle length, the needle insertion depth, and the needle insertion angle, the LED array 118 can have, for example six LEDs, e.g., a red LED and a green LED for each of needle length, needle insertion depth, and needle insertion angle, respectively.

In some embodiments, a first step in a needle insertion process can comprise measuring the length of the needle to be used during a procedure. In some embodiments, the system can generate an audio command that will instruct the user to measure the length of the needle. In some embodiments, the device may, alternatively or additionally, instruct the user with a visual indicator, for example by illuminating a letter on the device (e.g., "L" for length), for example using the LED array 118. In some embodiments, the apparatus 100 may display relevant instructions on the display 116. Having the user measure the needle can allow the device to be suitable for use with a wide range of needle lengths. In some embodiments, a user can insert a needle through the needle measurement hole 140. When the user inserts the needle into the needle measurement hole 140, the needle can push the needle guide 112 along the first track 132 inside the swing arm 104. The hilt sensor 142 (e.g., a momentary switch) can be depressed when the needle is fully inserted into the swing arm 104 (into the needle measurement hole 140) and can thereby cause the device to determine the length of the needle. In some embodiments, the apparatus may be configured to work with needles of at least a minimum size and no more than a maximum size. For example, a minimum size can be about 1 cm, about 2 cm, about 3 cm, about 4 cm, about 5 cm, or more.

In some embodiments, the apparatus 100 can prompt the user to find the depth of the target (e.g., vein). The system can include illumination, sounds, and so forth to aid the user in setting the target depth, in a manner similar to that described above with respect to measuring the needle length. Notably, however, the device may not have an automatic insertion depth measurement as it does for the needle length measurement. Rather, the user can measure the target depth using an ultrasound probe that can be inserted into the cavity 106 of the apparatus 100. In some embodiments, a user can input the target depth by sliding the insertion depth slider 114 along the second track 134. The second track 134 can have sensors embedded thereon that can be used by the apparatus 100 to detect the placement of the insertion depth slider 114. After the user sets the insertion depth, the user can confirm that insertion depth using the user input button 144, for example. In some embodiments, an LED corresponding to the insertion depth can be illuminated on the LED array 118. For example, if the insertion depth is within an allowable range (e.g., about 1 mm, more than about 1 mm, about 2 mm, more than about 2 mm, about 3 mm, more than about 3 mm, about 4 mm, more than about 4 mm, 5 mm, or more than about 5 mm), the central processing unit may cause a green LED associated with the depth to illuminate (for example, by the letter "D" as shown in FIG. 6E). If the insertion depth is outside an allowable range, the CPU may cause a red LED to illuminate instead. In some embodiments, the apparatus 100 can communicate wirelessly with an ultrasound probe and can receive the depth from the ultrasound probe instead of the user inputting the depth. In some embodiments, the apparatus 100 can be motorized to set insertion parameters automatically.

In some embodiments, the user can set a needle insertion angle by rotating the swing arm 104 relative to the base 102 using the angle adjustment knob 110. In some embodiments, the swing arm 104 can include a display 116 that can be configured to show the current angle of the swing arm 104. The user can adjust the angle of the swing arm 104 until the display indicates the desired angle. The user can confirm the needle insertion angle using the user input button 144. In some embodiments, the apparatus 100 can be configured to calculate a target angle. The display 116 can be configured to show a target angle. In some embodiments, the display 116 can include an indication of the target angle, an indication of the current angle, and/or a relative positioning indicator that can help the user adjust the apparatus 100 to the target insertion angle. The angle can be measured using the active angle sensor arm 130 and passive angle sensor plate 128 described above. In some embodiments, the apparatus 100 can illuminate an LED, make a sound, and/or provide another indication to the user when the target angle is reached. In some embodiments, the display 116 can be configured to display one or more arrows, circles, and so forth to indicate a direction the user should move the swing arm 104 to reach the target angle. The display 116 can be configured to show a circle, line, or other visual indicator that the user has reached the target angle. In some embodiments, the number of lights or similar can be used to indicate how far the current angle is from the target angle. As with the needle length and needle insertion depth, the system can be configured to light an LED in the LED array 118 based on the needle insertion angle setting. For example, if the insertion angle is too small or too large, the central processing unit can cause a red LED in the LED array 118 associated with the needle insertion angle to illuminate. On the other hand, if the needle insertion angle is within an allowable range, the system can illuminate a green LED associated with the needle insertion angle (e.g., an LED near the letter "A" in FIG. 6E).

Figure 7A:
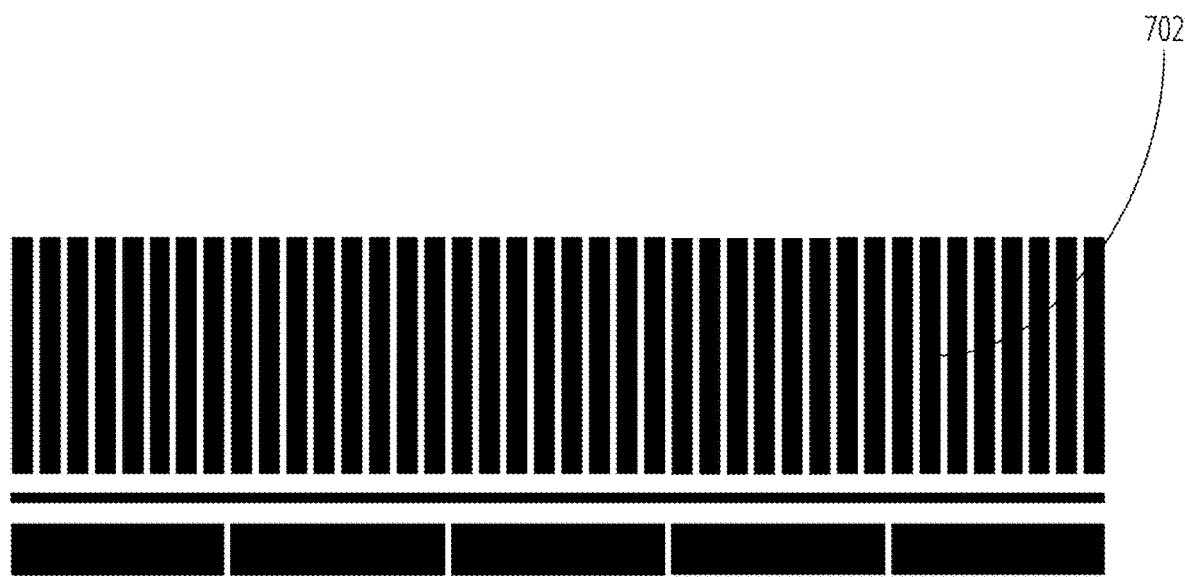
FIGS. 7A-7D show examples of electrodes for position and/or angle sensing according to some embodiments.
Figure 7B:
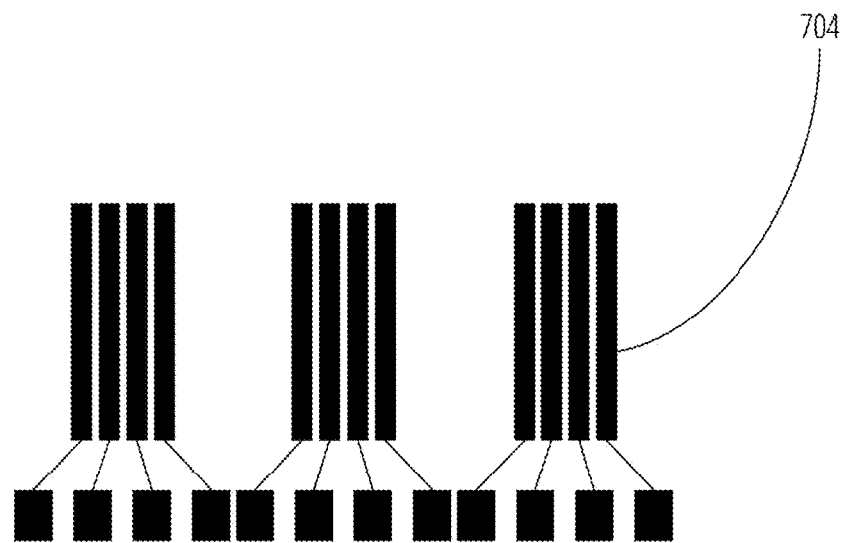
Figure 7D:
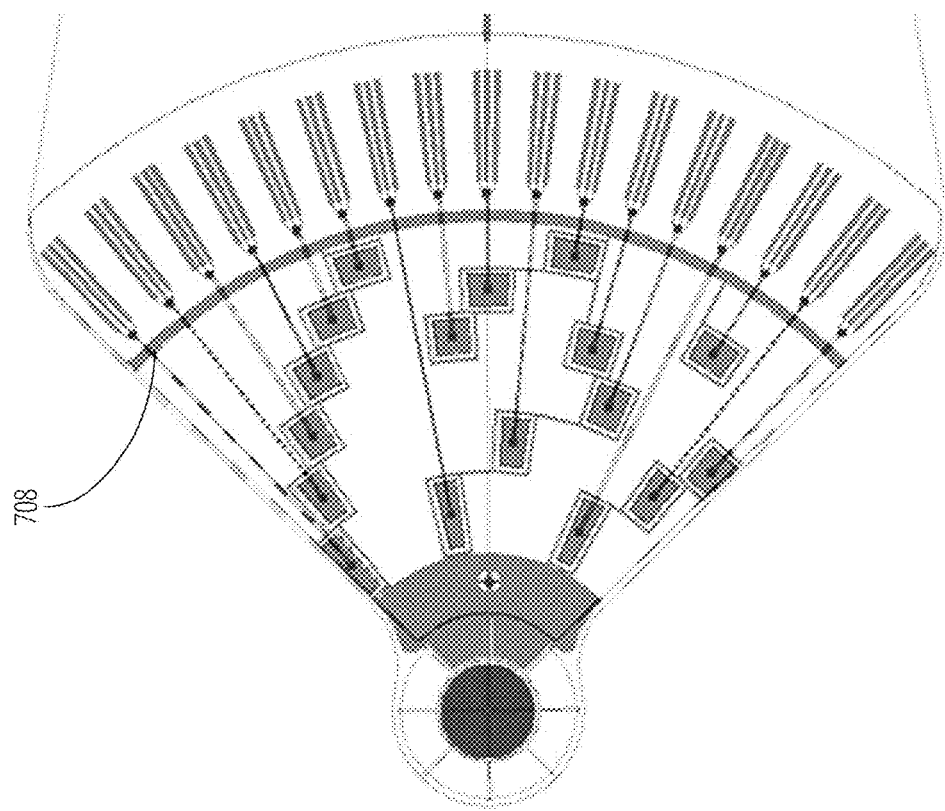
Figure 7C:
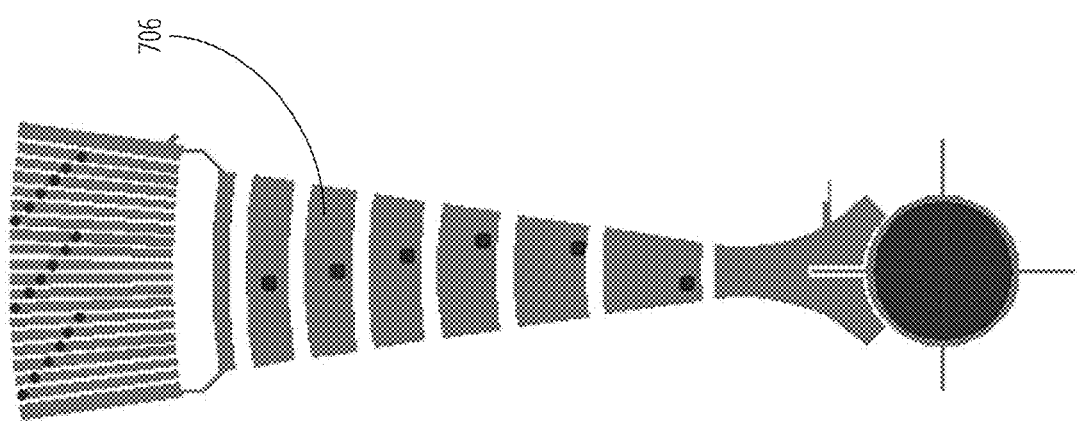

FIGS. 7A and 7B show an example linear sensing circuitry according to some embodiments. The electrodes 702 shown in FIG. 7A can be included on the first track 132 and/or the second track 134 and be used for detecting the position of the needle guide 112 and/or the insertion depth slider 114. The electrodes 704 can be included as part of the needle guide 112 and/or the insertion depth slider 114. The electrodes 702 can be active (e.g., connected to a power source) while the electrodes 704 can be passive (e.g., not normally connected to a power source). FIGS. 7C and 7D show example angular sensing circuitry according to some embodiments. The electrodes 706 can part included on a swing arm 104 as all or part of the active angle sensor arm 130. The electrodes 706 can be normally powered (e.g., connected to a power source). The electrodes 708 can be disposed on the passive angle sensor plate 128 and can be passive electrodes (e.g., not ordinarily connected to a power source). As discussed briefly above, the electrodes 702, electrodes 704, electrodes 706, and electrodes 708 can be used for detecting linear and/or angular position using capacitance, resistance, connectivity, and so forth. In some embodiments, the length of a passive sensor, e.g., having electrodes 704 or electrodes 708 disposed thereon, can be relatively small and/or can consist of multiple frames. In some embodiments, a coding scheme can be used to extend the measurement range and/or to increase the precision and/or accuracy of the measurements. In some embodiments, multiple linear sensors can share a common transmit driver, which can reduce power and input/output requirements. In some embodiments, the sensors described herein can support a high slew rate, for example using velocity detection. In some embodiments, the sensors herein can be configured to switch between absolute and relative measurement modes.

Figure 8:
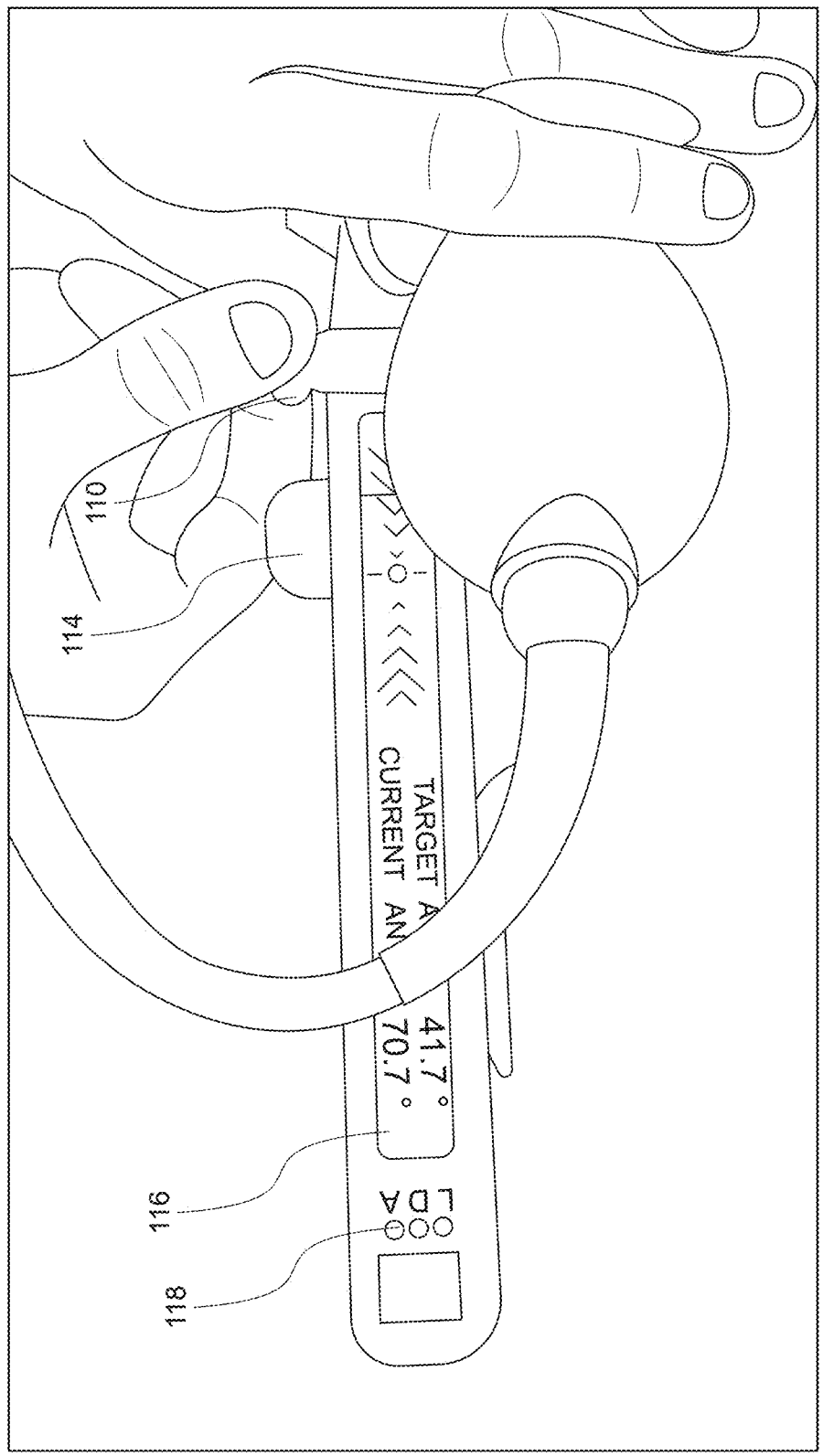
FIG. 8 is a view of an example insertion apparatus during use according to some embodiments.

FIG. 8 shows an example embodiment of an apparatus 100 in which the user is setting the needle insertion angle by adjusting the angle adjustment knob 110. As shown in FIG. 8, an LED in the LED array 118 labeled "L" is illuminated, indicating the needle length has been measured, and an LED in the LED array 118 labeled "D" is illuminated, indicating that the needle insertion depth has been set. The display 116 displays a target angle (here, 41.7 degrees) and the current angle (70.7 degrees). The display 116 also includes arrows and a circle near the distal end (i.e., near the angle adjustment knob 110) that indicates the user should reduce the angle of the swing arm 104.

The LED array 118 may have functions in addition to or as an alternative to display error and success states. For example, LEDs in the LED array 118 can flash to indicate which step of a process the user is at. For example, one or more LEDs can flash under the "L" in FIG. 6E when the user is supposed to perform a needle length measurement procedure. One or more LEDs can flash under the "D" when the user is supposed to perform a procedure for setting the needle insertion length. One or more LEDs can flash under the "A" when the user is supposed to perform a procedure for setting the needle insertion angle. As discussed above, the number of LEDs in the LED array 118 can vary depending on the number of adjustments, settings, and so forth available to the user. In some embodiments, the apparatus 100 may not include a LED array 118 and may instead rely on the display 116. In some embodiments, the apparatus 100 may not include the display 116 and may instead rely on the LED array 118. In some embodiments, the system may not include the display 116 or the LED array 118 and can instead rely on alternative ways of providing guidance to the user, such as using audible feedback.

Stabilization

The apparatus 100 above can be used to accurately insert a needle into a patient. However, setting the insertion depth, angle, and needle length appropriately does not guarantee successful insertion, and difficulties can be encountered in practice. For example, patients can move, providers can apply differing amounts of pressure to the relevant area (e.g., to the patient's forearm), and so forth. The depth of the target can vary as the provider pushes on the patient because soft tissue is pliable. For example, if a provider pushes down relatively hard on the patient, a vein can be at a shallower depth than if the provider presses relatively gently. Thus, if a physician applies more or less pressure to the patient (e.g., by pressing down an ultrasound probe and/or by pushing down on the apparatus 100), the appropriate insertion depth can change.

Figure 9B:
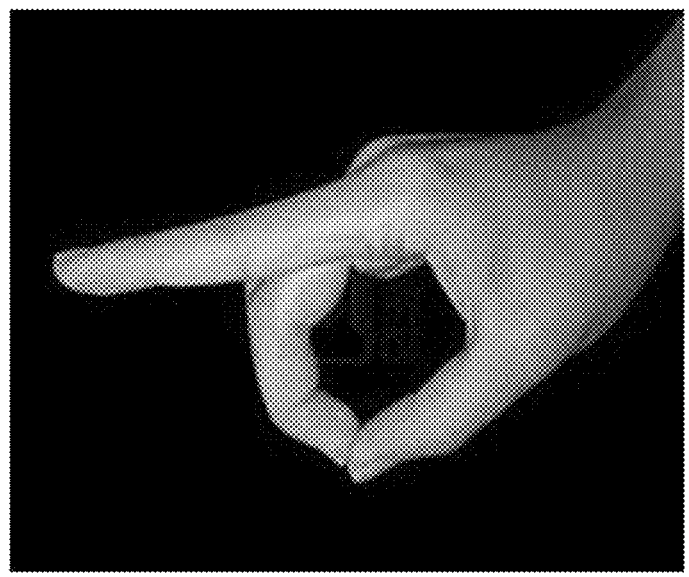
FIGS. 9A and 9B show example grips that a user can use when using some embodiments of an insertion apparatus.
Figure 9A:
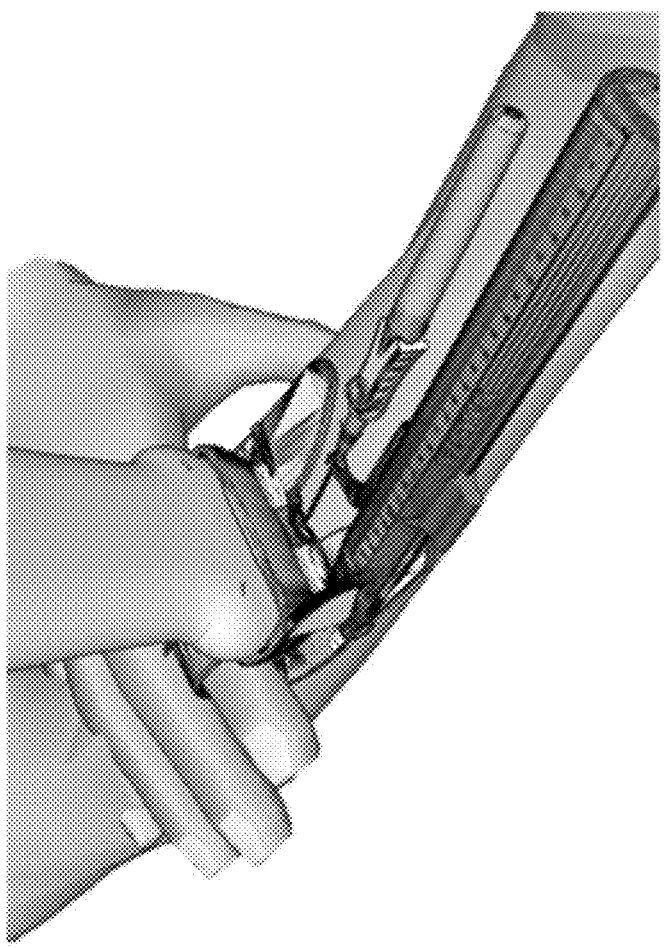

Accordingly, some embodiments of the apparatus 100 can include a finger hole 108, which can help the provider to hold the apparatus 100 against the patient in a more consistent manner. As shown in FIG. 9A, a provider can place their index finger in the finger hole 108 and can place their other fingers adjacent to the finger hole 108. In some procedures, for example when inserting a needle into an arm or leg, the provider can place their thumb on the other side of the patient's limb, for example as illustrated in FIG. 9B. It will be appreciated that FIGS. 9A and 9B are merely examples, and a provider may grip a patient and or apparatus in other ways as appropriate for the patient and the procedure. For example, the grip can be modified for pediatric patients. Advantageously, the apparatus 100 can facilitate a firm grip and steady placement in a wide variety of usage scenarios.

Figure 10B:
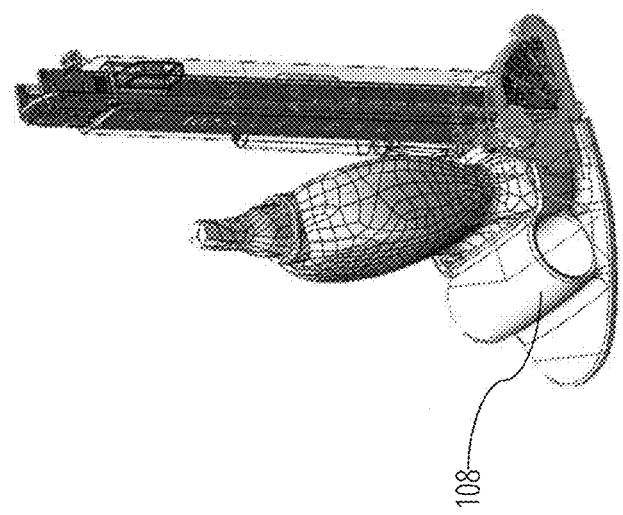
FIGS. 10A-10D are views of example embodiments of insertion apparatuses having different finger holes.
Figure 10D:
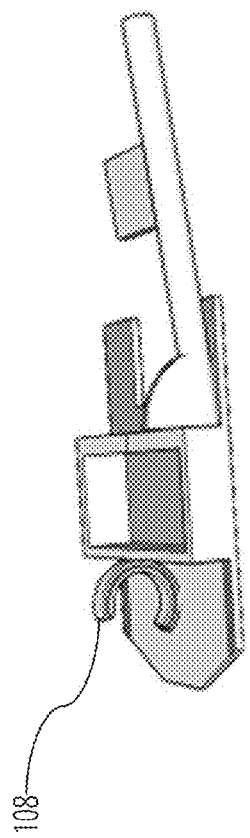
Figure 10A:
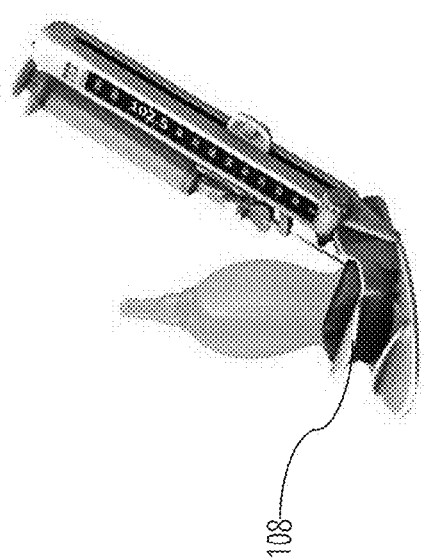
Figure 10C:
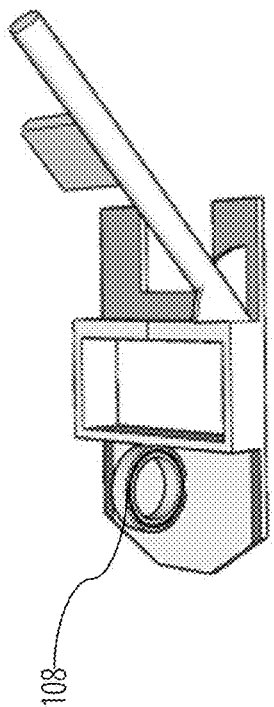

In some embodiments, the finger hole 108 can be open or closed. For example, the finger hole 108 can be a cylinder open on both ends. In other embodiments, the finger hole 108 can be open, as shown in FIG. 10A. An open design may enhance user comfort and/or be usable by users with a wider range of finger sizes. In some embodiments, the finger hole 108 can extend substantially the entire width of the base 102, while in other embodiments the finger hole 108 can have a relatively short length, for example half the width of the base 102 or less, such as about the width of a ring. FIGS. 10A-10D illustrate various embodiments of the finger hole 108. Different embodiments of the finger hole 108 can be desirable depending on the provider's preferences, the type of procedure being performed, the type of patient (e.g., adult or pediatric), and so forth. The finger hole 108 can be placed at various locations on the base 102. For example, the finger hole 108 can be placed at the front, rear, on a side, and so forth, and could be rotated (e.g., rotated 90 degrees) relative to the orientation shown in the figures.

Because the apparatus 100 can enable a provider to maintain a firm, stable placement with respect to the patient, the apparatus 100 can move as the patient moves in a manner that maintains the placement of the apparatus 100 and that preserves the insertion depth and/or insertion angle. Accordingly, the provider can have a greater chance of successfully placing the needle in the desired location without repeated attempts.

Figure 11:
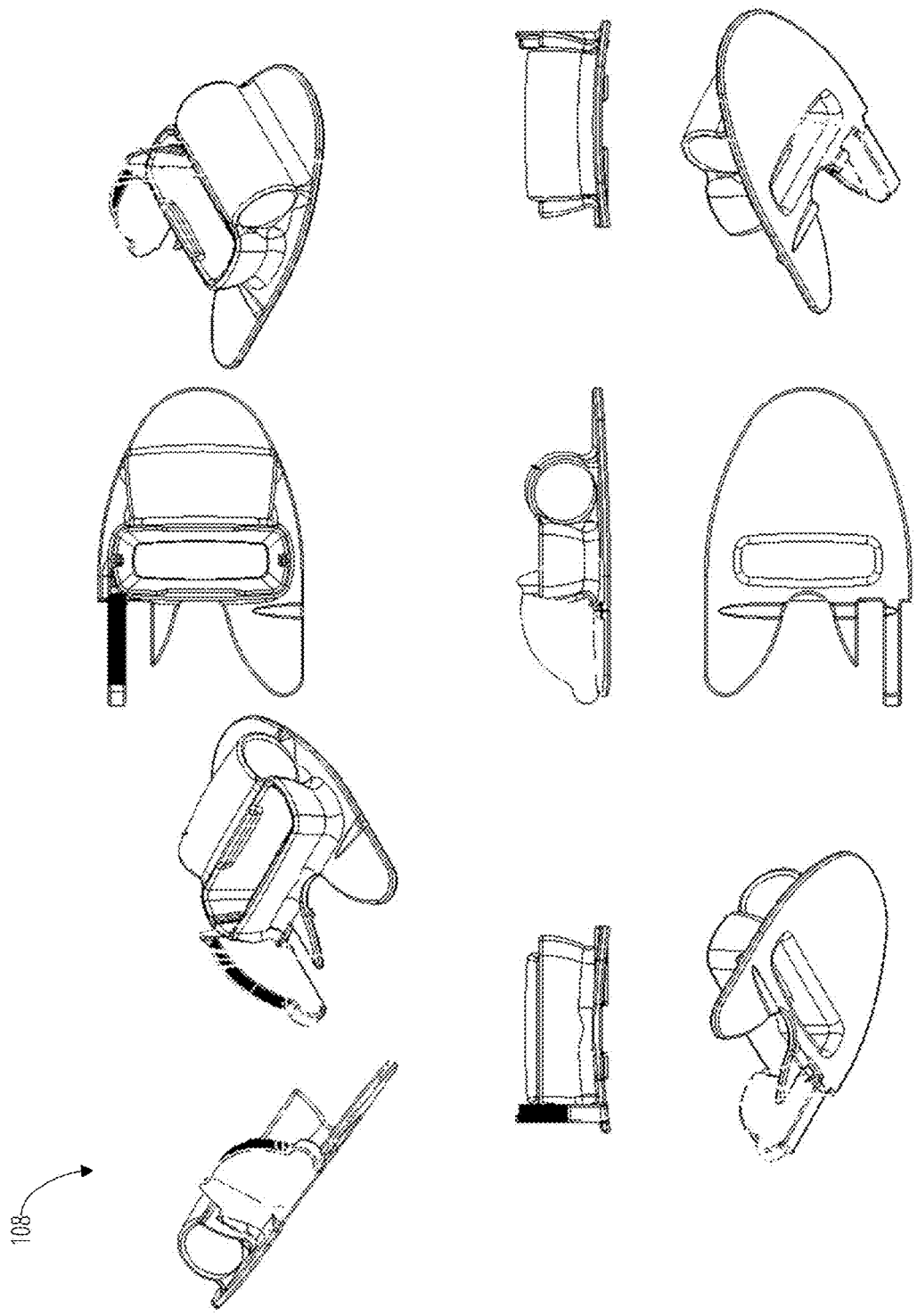
FIG. 11 shows views of a base of an insertion apparatus according to some embodiments.

The shape of the base 102 can also play a role in the stability of the apparatus 100. In some embodiments, the base 102 of the apparatus 100 can be curved or flat. For example, a curved base 102 can be desirable when performing an insertion into an arm, leg, and so forth, while a flat base 102 can be desirable when performing an insertion into, for example, a patient's chest or other relatively flat area. FIG. 11 shows various views of a base 102, which can have a flat bottom or a curved bottom.

Sterilization

The apparatus 100 is generally for use in procedures that involve puncturing a patient's skin. Thus, it can be important to ensure that the apparatus 100 and any associated components that come into contact with the patient are sterile. In some cases, some components used in a procedure may not be sterile, such an ultrasound probe and its associated cord. Measures can be taken to protect the patient from exposure to non-sterile components.

Figure 12A:
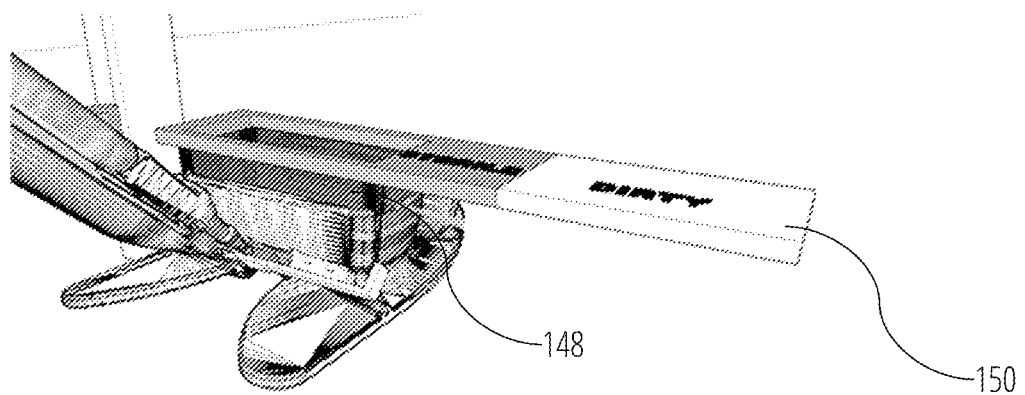
FIGS. 12A and 12B show views of a sterile bag and sterile handle according to some embodiments.
Figure 12B:
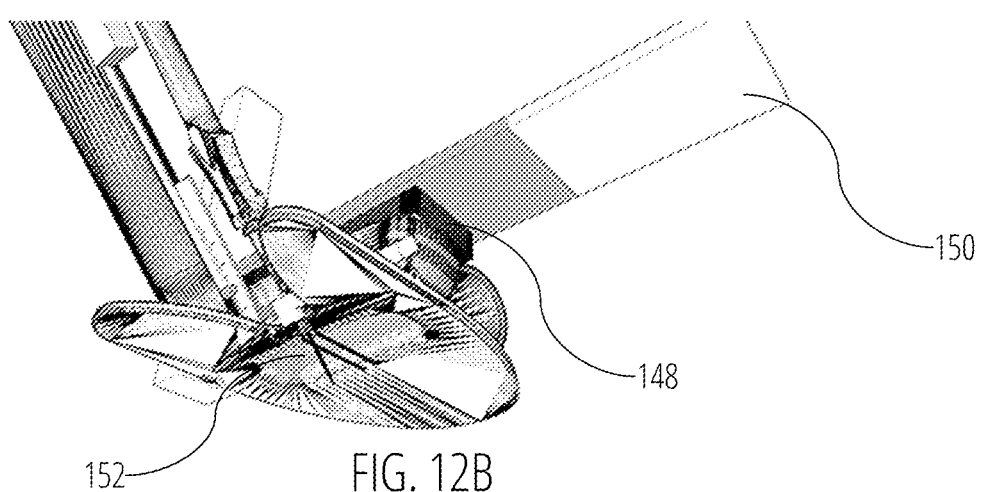

As discussed above, the apparatus 100 can be used in conjunction with an ultrasound probe. In some cases, the ultrasound probe can be wired and have a cord associated therewith, while in other cases, the ultrasound probe can be wireless. In some cases, the ultrasound probe can be considered non-sterile. In some cases, the ultrasound probe cord can be considered non-sterile. Accordingly, it can be important to prevent the non-sterile components from coming into contact with objects that should be kept sterile (e.g., objects that will be placed on the patient, such as the apparatus 100). In some embodiments, the apparatus 100 can comprise a bag 148 as shown in FIGS. 12A and 12B. In some embodiments, the apparatus 100 can comprise a sterile handle 150. In some embodiments, the bag 148 can be attached to the sterile handle 150. The sterile handle 150 can have a non-sterile portion and a sterile portion. In some embodiments, the bag can be open at both ends. In some embodiments, one end of the bag 148 can be attached to the cavity 106 and the other end can be attached to a tab. In some embodiments, the bag can be attached to the cavity 106. In some embodiments, the sterile handle 150 can include a wire that can be used to tie off the end of the bag 148.

A provider can place the ultrasound probe (and, if applicable, the cord for the ultrasound probe) into the bag. The bag can be affixed at one end to the cavity 106, for example to the rim of the cavity 106. In some embodiments, the apparatus 100 can include a protective sterile film 152. The protective sterile film 152 can provide a barrier between the ultrasound probe and the patient's skin. In some embodiments, a user can provide ultrasound gel into the cavity 106 prior to inserting the ultrasound probe. For example, the provider can dispense an amount of ultrasound gel on top of the protective sterile film 152 and then insert the ultrasound probe into the cavity 106.

Figure 12C:
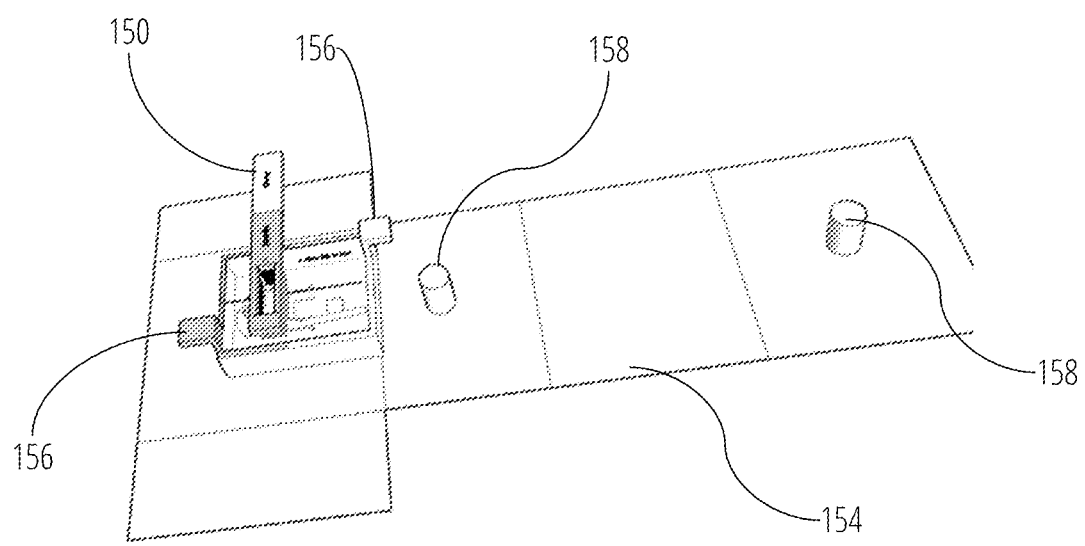
FIG. 12C is a view of an example embodiment of sterile packaging.

As shown in FIG. 12C, in some embodiments, the apparatus 100 can be inside a sterile packaging 154. The sterile packaging 154 can include sterile packaging tabs 156 and/or sterile packaging posts 158. The sterile packaging 154 can include sterile packaging tabs 156 and/or sterile packaging posts 158 can be used to, for example, aid in positioning the cord of an ultrasound probe.

As discussed above, the apparatus 100 can include a variety of active components such as the active angle sensor arm 130, the display 116, LED array 118, linear position sensors, batteries, processing hardware, memory hardware, printed circuit boards, and so forth. Preferably, some of these components can be reused, which can reduce the cost associated with using the apparatus 100. However, it is important that any reusable components be kept out of contact with the patient.

Figure 13:
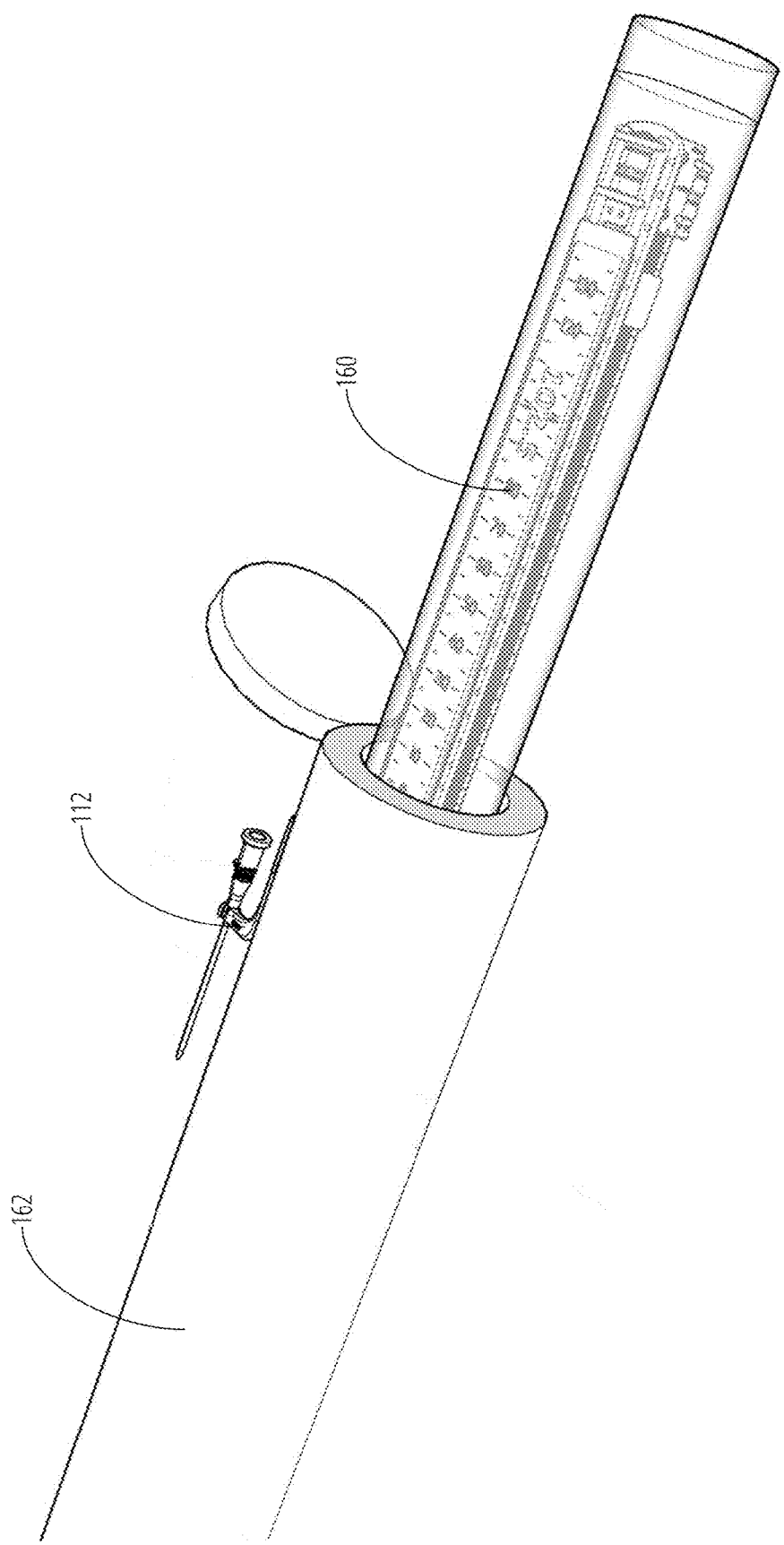
FIG. 13 is a view of an example embodiment of a reusable electronics package and disposable electronics package sleeve.

FIG. 13 depicts an example embodiment of a swing arm 104 in which an electronics package 160 can be placed inside an electronics package sleeve 162. The electronics package 160 can be kept in isolation from the patient, which can enable reuse of the electronics package 160. The electronics package sleeve 162 can come into contact with the patient, with body fluids, and so forth, and thus can be discarded after each use.

The apparatus 100 described above can be designed to accommodate a range of needle lengths, insertion depths, and insertion angles. However, in some embodiments, such flexibility may not be needed. Thus, some embodiments of the apparatus 100 may not allow for adjustment of all three parameters. Such limitations can have several advantages. For example, a device with fewer adjustable parameters can be easier to use, and thus may reduce errors, reduce the time needed to use the apparatus, and so forth. A device with fewer adjustable parameters can be cheaper to manufacture. For example, a device that does not allow for adjusting the needle length can cost less to manufacture because hardware specific to measuring the needle length can be omitted. Similarly, cost savings and reduced device complexity can be realized by, for example, limiting the insertion angle.

As one example, an apparatus 100 can be configured for inserting pediatric IV catheters. In some embodiments, needle length can be fixed. In some embodiments, diameter can be fixed. In some embodiments, the electronics of the apparatus 100 can be pre-programmed to work with a particular needle length or a particular range of needle lengths. For example, if a user wants to insert an 18 gauge IV catheter using a needle of a known length L, the apparatus 100 can be configured so that the user can select the length L, for example by pressing a button or adjusting a slider on the apparatus 100 until the display 116 indicates the appropriate needle length L.

Figure 14:
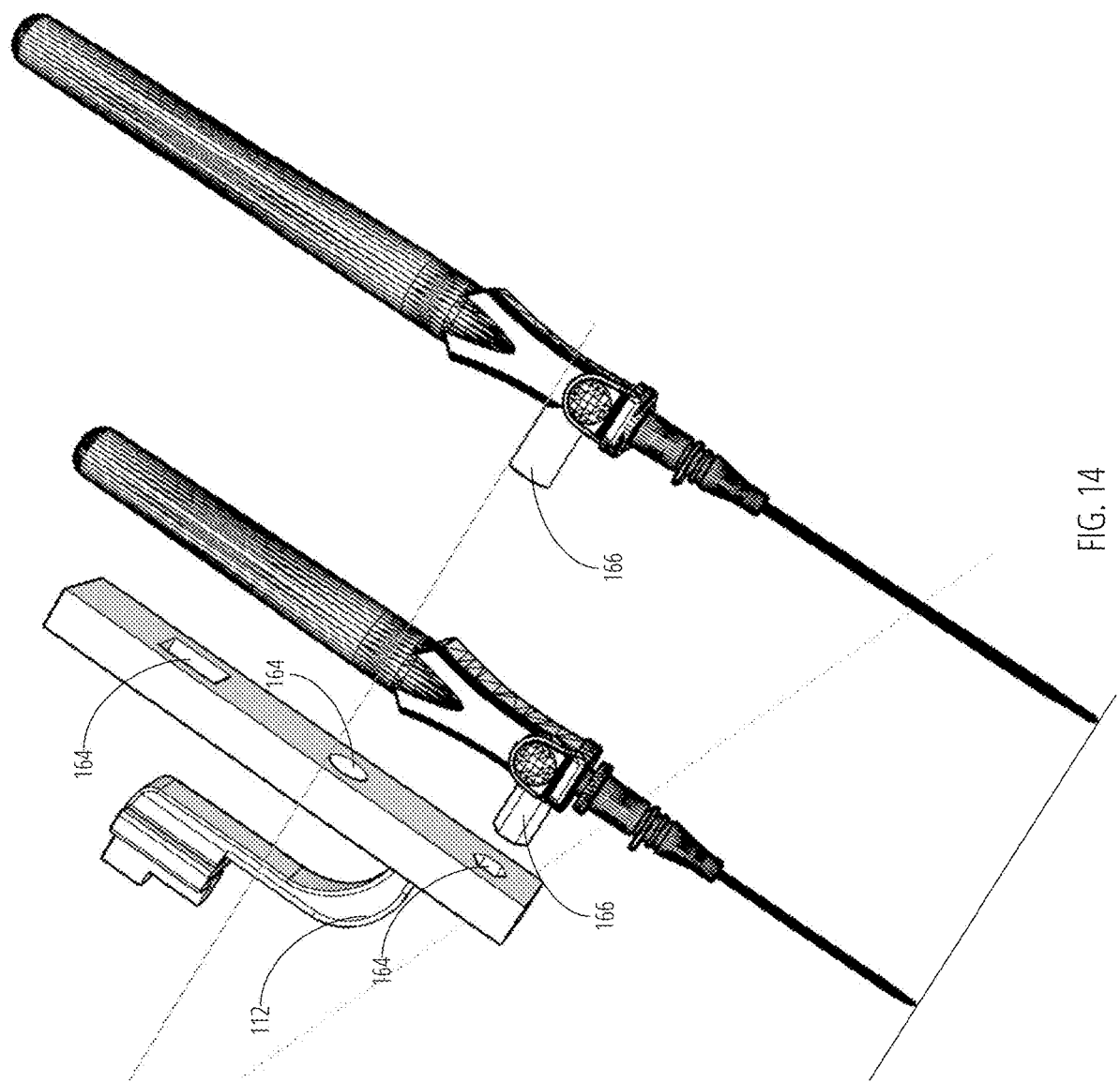
FIG. 14 is a view of an example needle holder and needles according to some embodiments.

In some embodiments, a needle guide 112 can be configured to receive a needle of a particular length. For example, a needle can include a side port 166, and the needle guide 112 can be configured to include receivers 164 that the side port 166 can fit into. In some embodiments, the shape of the side port can indicate one or more properties of the needle such as the needle length and/or the needle gauge, and the apparatus 100 can be configured to recognize the needle length, gauge, etc., based on the receiver 164 into which the port was inserted (for example, using sensors embedded in the receivers 164). In some embodiments, the shape of the receiver 164 can be circular, rectangular, hexagonal, and so forth. In some embodiments, receivers 164 can be placed on the needle guide 112 such that, regardless of the length of the needle, the tip of the needle is always at the same place as shown in FIG. 14.

In some embodiments, the apparatus can be pre-configured to support a fixed number of needle lengths. For example, the user may select an appropriate needle length using the user input button 144 until the display 116 shows the correct needle length.

In some embodiments, an apparatus 100 can be configured so that the needle always pierces the patient's skin at a fixed distance from the ultrasound probe, and the insertion depth can be controlled by adjusting the insertion angle. In some embodiments, instead of adjusting the insertion angle, the insertion angle can be fixed and the insertion depth can be adjusted by modifying the distance between the insertion point and the ultrasound probe.

In some embodiments, a needle insertion point on the patient's skin can be fixed. In some embodiments, the needle insertion depth can vary. In some embodiments, an insertion apparatus can be a mechanical device (i.e., a device without electronics). A mechanical device can have several advantages. For example, a mechanical device can be relatively simple and cheap to manufacture.

In some embodiments, a needle can be inserted at a fixed distance x/2 away from the ultrasound probe, as illustrated in FIG. 13. The needle can be raised a distance x from the ultrasound probe, such that the angle of the needle above the skin is the same as the angle of the needle below the skin and the height of the needle above the skin corresponds to the distance of the needle below the skin when the needle is inserted such that the tip of the needle is below (e.g., directly below) the ultrasound probe.

Figure 15:
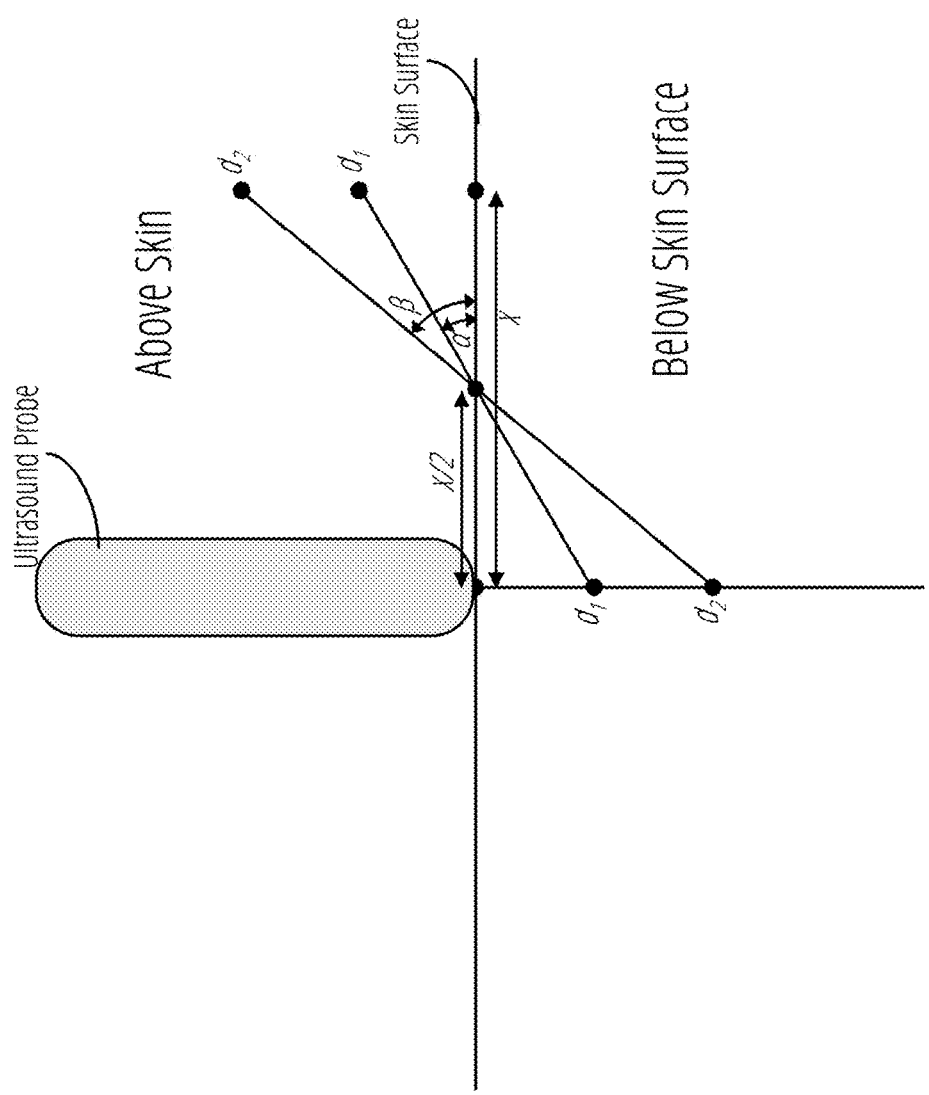
FIG. 15 is a diagram illustrating needle insertion geometry with a fixed needle insertion point according to some embodiments.
Figure 16:
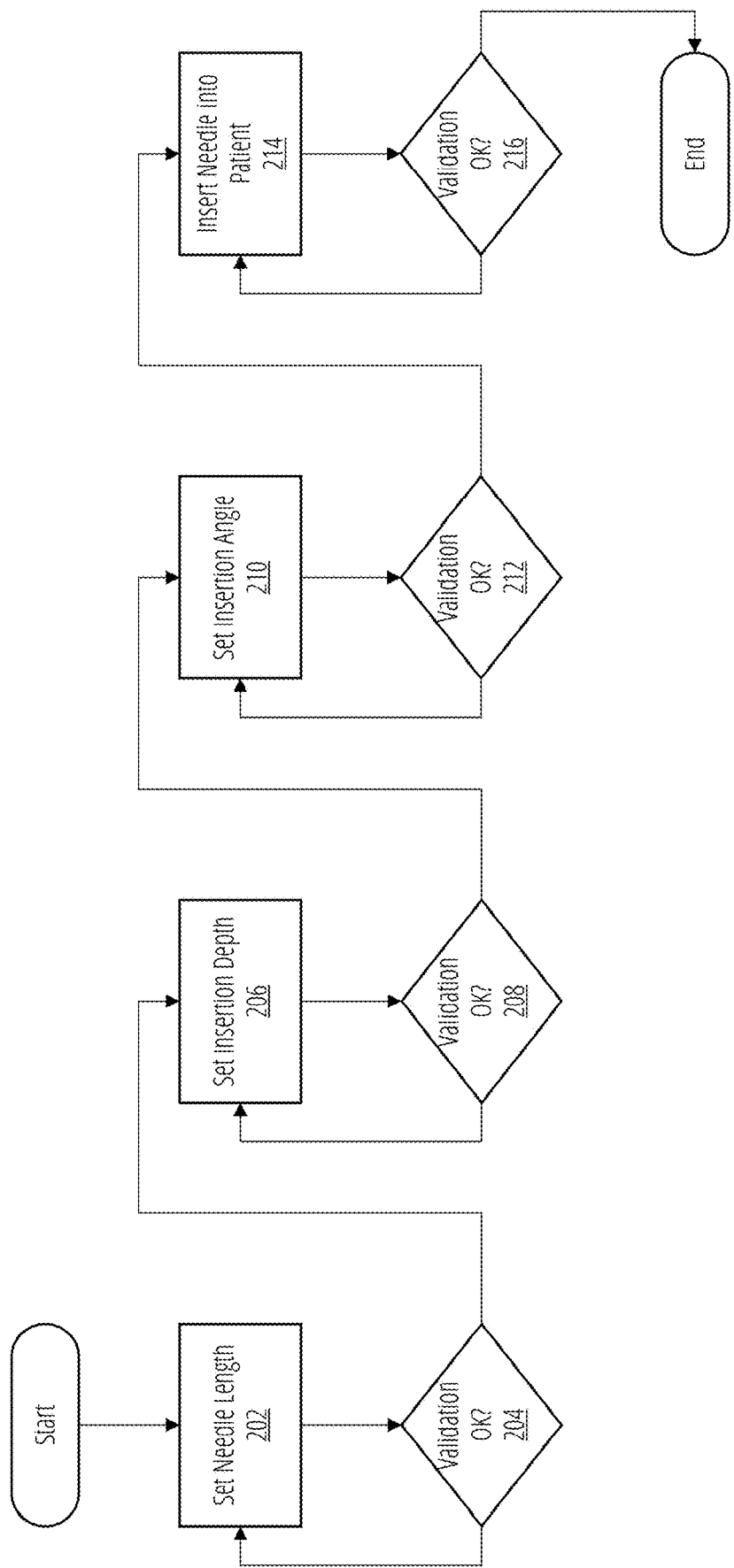
FIG. 16 is a block diagram of a process for performing an insertion procedure according to some embodiments.

For example, as shown in FIG. 15, a needle a horizontal distance x away from an ultrasound probe can be inserted to a first depth $d_1$ by raising the needle to a height $d_1$ above the skin of the patient and inserting the needle at an angle $\alpha$ such that the needle contacts the skin at x/2. The angle $\alpha$ can be determined by $\alpha = \tan^{-1} 2d_1/x$. Similarly, a needle can be inserted to a second depth $d_2$ by raising the needle to a height $d_2$ above the surface of the patient's skin and inserting the needle at an angle $\beta$ such that the needle contacts the skin at the point x/2. That is, the point x/2 where the needle contacts the skin can operate as a pivot point.

It will be appreciated such a configuration is not necessary. For example, a configuration may not use congruent triangles. In some embodiments, the insertion point can be closer to the ultrasound probe or farther from the ultrasound probe.

FIGS. 16-19 show example processes for performing a needle insertion procedure using an insertion device according to some embodiments herein. Starting with FIG. 16, an insertion process can include, at block 202, setting a needle length. At block 204, the device can validate the needle length. If the validation fails, the device can prompt the user to measure the needle length again. If the validation passes, the device can prompt the user to set the insertion depth of the needle at block 206. At block 208, the device can validate the insertion depth. If the validation fails, the device can prompt the user to set the insertion depth again. If the validation passes, the device can advance the user to block 210, where the user can set the insertion angle. At block 212, the device can validate the insertion angle. If the insertion angle fails the validation, the device can prompt the user to set the insertion angle again. If the validation passes, the user can advance to block 214, where the user can insert the needle into the patient. At block 216, the device can validate the insertion procedure. If the validation passes, the process can be complete. If the validation fails, the user may try inserting the needle again. In some cases, the user may abandon the procedure and start over. In some embodiments, the apparatus 100 can be configured to alert the user when the user inserts the needle beyond the set insertion depth.

Figure 17:
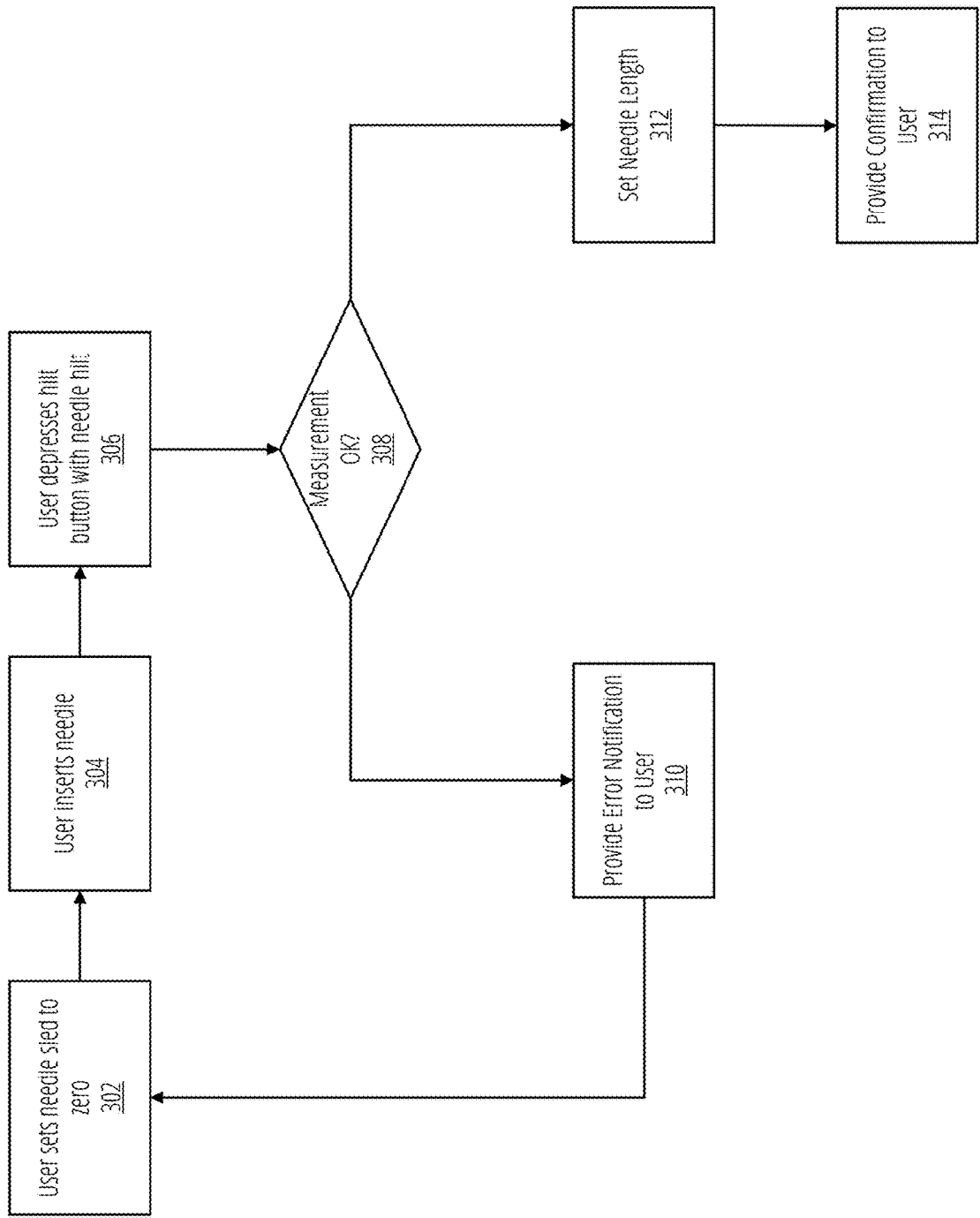
FIG. 17 is a block diagram of a process for performing a needle length measurement procedure according to some embodiments.

FIG. 17 depicts an example process for setting a needle length according to some embodiments. The process depicted in FIG. 17 may be carried out, for example, as part of blocks 202 and 204 in FIG. 16. At block 302, the user can set the needle sled to zero. The user can then, at block 304, inset the needle into the device, for example through the needle measurement hole 140. At block 306, the user can depress the hilt sensor 142 with the needle hilt when the needle is fully inserted into the needle measurement hole 140. The device can be configured to determine the length of the needle when the hilt sensor 142 is depressed. At decision point 308, the device can determine if the needle length measurement is acceptable. For example, the system can determine if the needle length is within an allowable range. For example, in some embodiments, a device can be configured to require a minimum needle length. In some embodiments, a device can be configured to accept a maximum needle length. If the measurement is not okay (e.g., the needle length is too short, which may indicate that the hilt sensor 142 was improperly or accidentally triggered), the device can provide an error notification to the user at block 310, for example by displaying a message on the display 116, showing a red color on the LED array 118, playing a sound, and so forth, and the user can retry to needle measurement procedure. If, at decision point 308, the measurement is okay, the device can be configured to store the needle length at block 312, for example storing the needle length in on board memory. The device can, at block 314, provide an indication to the user that the needle length has been set successfully, for example by showing a message on the display 116, showing a green color on the LED array 118, playing a sound, and so forth.

Figure 18:
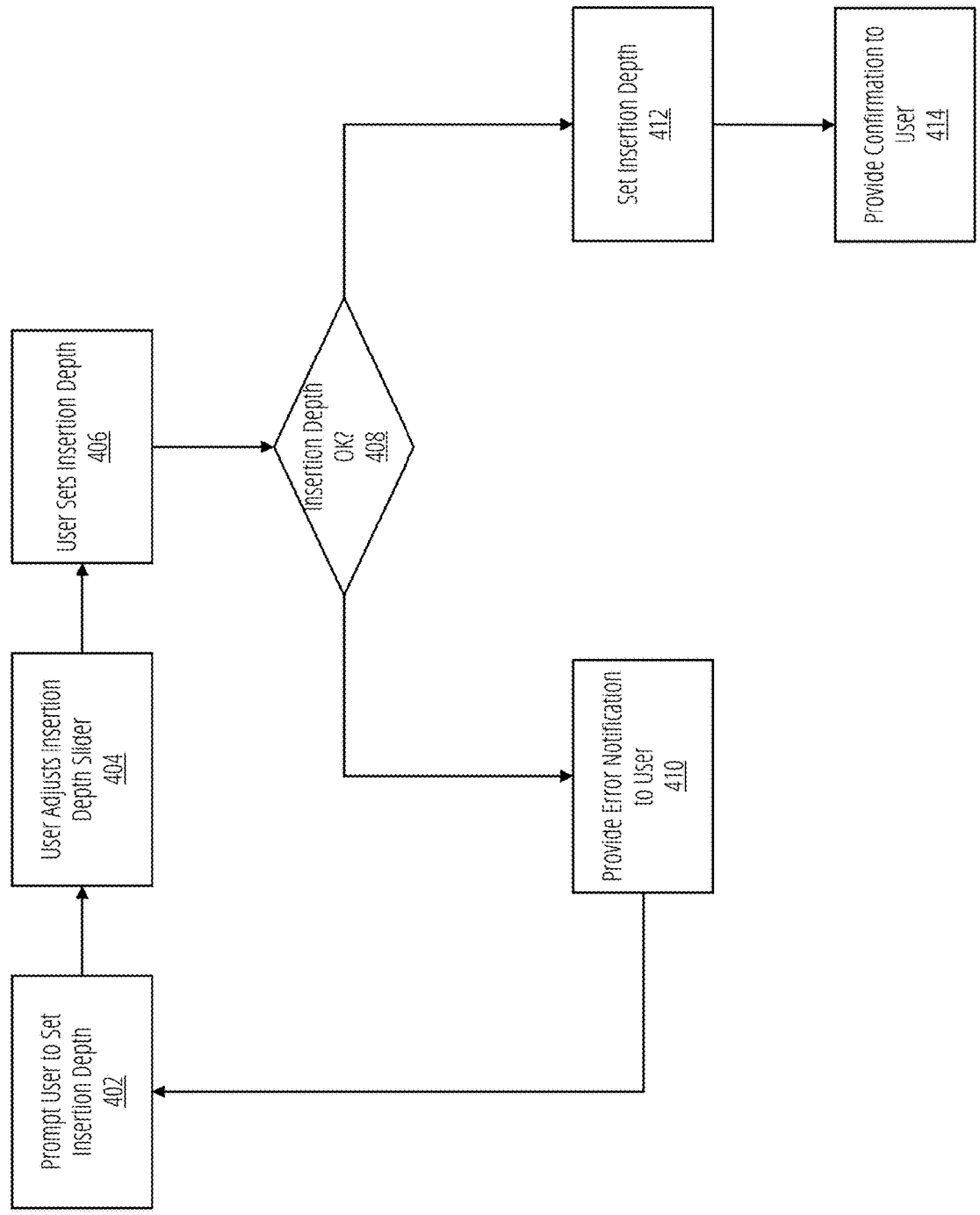
FIG. 18 is a block diagram of a process for setting a needle insertion depth according to some embodiments.

FIG. 18 depicts an example process for setting a needle insertion depth according to some embodiments. The process depicted in FIG. 18 may be carried out, for example, as part of blocks 206 and 208 of FIG. 16. At block 402, the device can prompt the user to set the insertion depth. The user can determine the insertion depth by, for example, placing an ultrasound probe in the cavity 106 of the apparatus 100 and measuring the depth to a target (e.g., a vein) inside the patient. The user can, at block 404, adjust the insertion depth, for example by adjusting the insertion depth insertion depth slider 114, and can then set the insertion depth at block 406. At decision point 408, the device can determine if the insertion depth is acceptable. For example, the device may be configured to allow insertion depths from a minimum value to a maximum value. If the insertion depth is outside the allowable range, the device can, at a block 410, provide an error notification to the user, for example by displaying a message on the display 116, showing a red color on the LED array 118, playing a sound, and so forth, and the user can retry to insertion depth setting procedure. If, at decision point 408, the insertion angle is acceptable, the device can be configured to store the insertion depth at block 412, for example in memory on board the device. The device can, at block 414, provide confirmation to the user that the insertion depth has been set successfully, for example by showing a message on the display 116, showing a green color on the LED array 118, playing a sound, and so forth.

Figure 19:
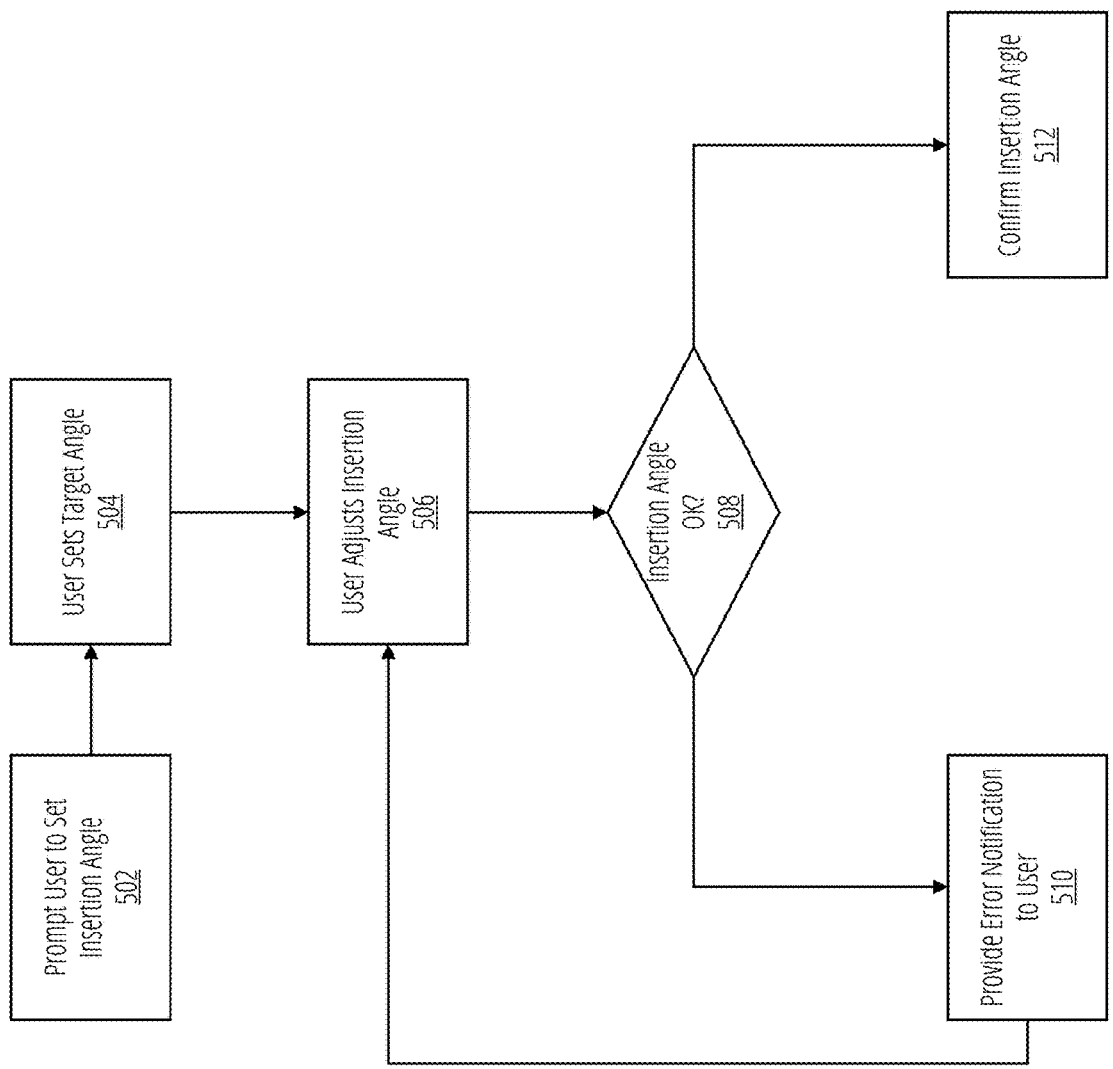
FIG. 19 is a block diagram of a process for a setting a needle insertion angle according to some embodiments.

FIG. 19 depicts an example process for setting a needle insertion angle according to some embodiments. The process depicted in FIG. 19 may be carried out, for example, as part of blocks 210 and 212 of FIG. 16. At block 502, the device can prompt the user to set the insertion angle. In some embodiments, at block 504, the user can input a target angle. In some embodiments, the target angle can be fixed. In some embodiments, the device can be configured to determine a target angle based in part on the insertion depth. At block 506, the user can adjust the insertion angle, for example by adjusting the angle adjustment knob 110. At decision point 508, the device can monitor the insertion angle and compare it to the target angle. If the mismatch between the insertion angle and the target angle exceeds a threshold amount (e.g., about 1 degree, about 2 degrees, about 5 degrees, about 10 degrees, or about 15 degrees), the system can provide a notification to the user at block 510 and the user can continue adjusting the insertion angle. If the insertion angle is acceptable (e.g., the difference between the insertion angle and the target angle is within the threshold amount), the system can, at block 512, provide a confirmation to the user. The error and confirmation notifications may be provided in the same or a similar manner as in FIGS. 17 and 18. In some embodiments, the display 116 can provide a visual indication of how far the insertion angle is from the target angle, as discussed above with reference to FIG. 8.

Figure 20:
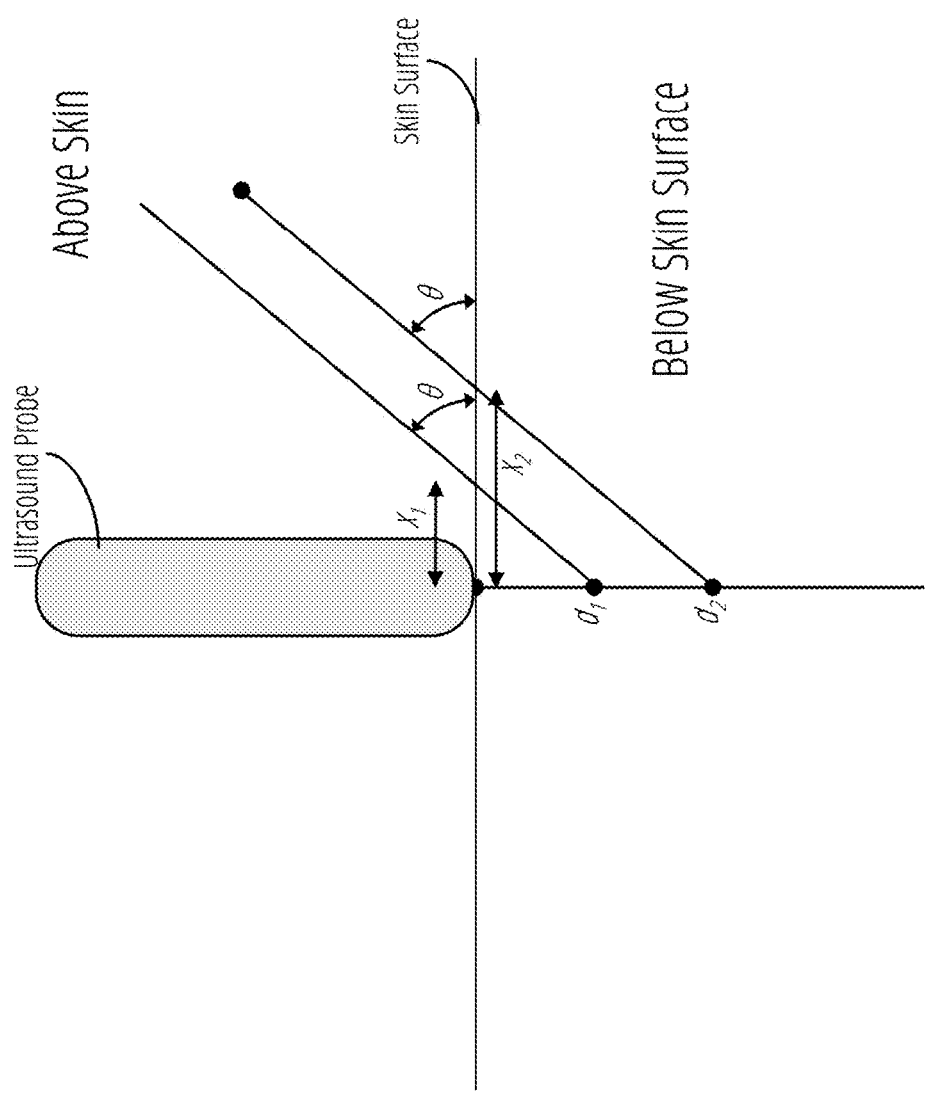
FIG. 20 is a diagram illustrating needle insertion geometry with a fixed needle insertion angle according to some embodiments.

In some embodiments, rather than adjusting the angle and using a fixed insertion point, an apparatus 100 can be configured to insert at a fixed angle θ and to control the needle insertion depth by altering the distance between the insertion point and the ultrasound probe. Thus, for example, to insert at a depth $d_1$ below the ultrasound probe as indicated in FIG. 20, the distance between the ultrasound probe and the needle insertion point can be $x_1 = d/\tan\theta$. The processes depicted in FIGS. 16-19 can be substantially similar for a fixed angle approach, with appropriate modifications. For example, rather than setting the insertion angle, a user would instead set the insertion distance (i.e., the distance between the ultrasound probe and the needle insertion point on the patient's skin).

In some embodiments, the insertion methods shown in FIGS. 15 and 20 can be carried out without the aid of electronic devices on board the apparatus 100. For example, markings on the apparatus 100 can be used to set and to monitor the angle, depth, and so forth. Advantageously, when the insertion angle or the insertion point is fixed, determining the appropriate value for an adjustable parameter can involve only simple trigonometry and relevant indicators or markings can be included on the device itself.

Other Example Apparatus Embodiments

Other embodiments of the apparatus discussed above are anticipated. For example, the needle holder, angle adjustment mechanism, needle support bracket, and so forth can be modified for various use cases without departing from the present disclosure.

Figure 21A:
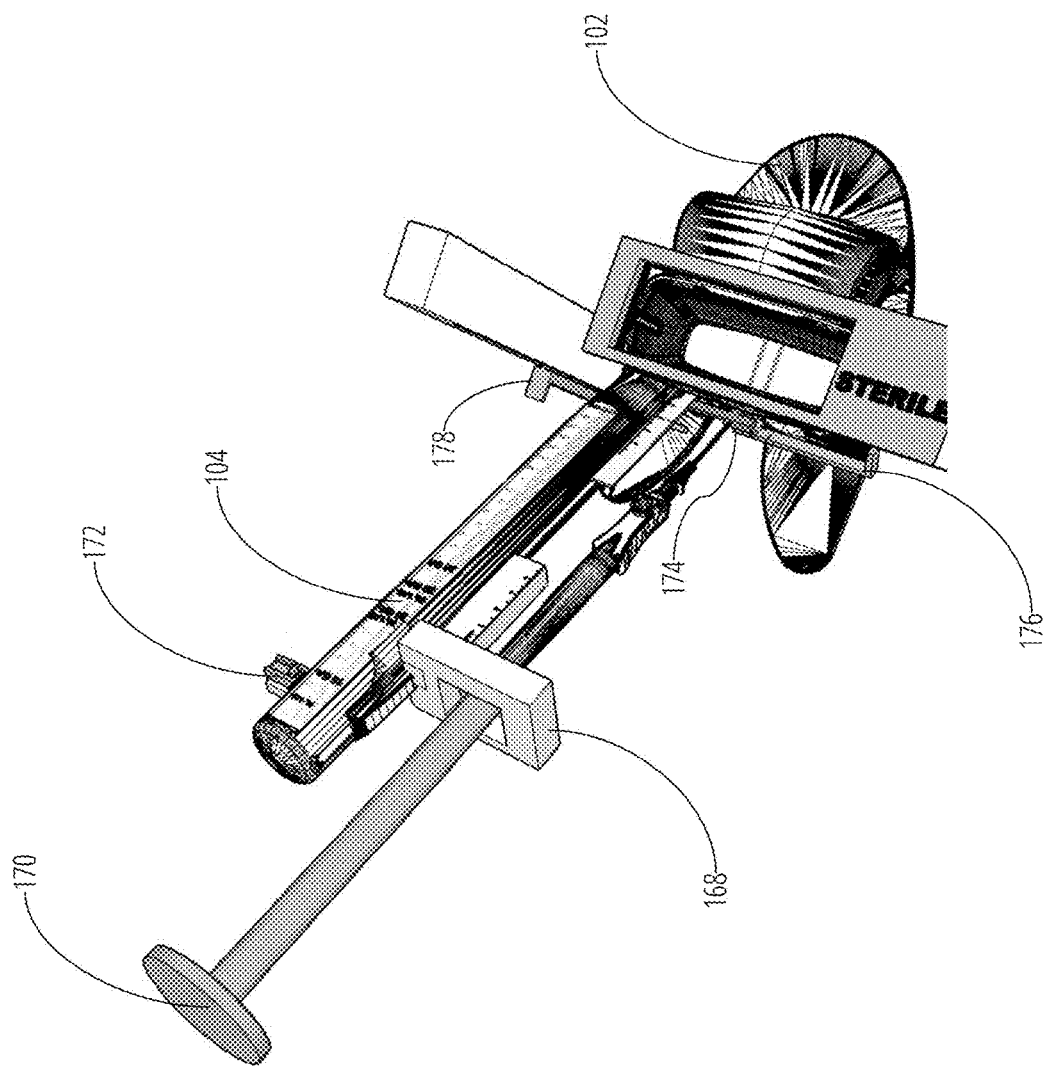
FIGS. 21A and 21B are views of an example embodiment of an insertion apparatus.
Figure 21B:
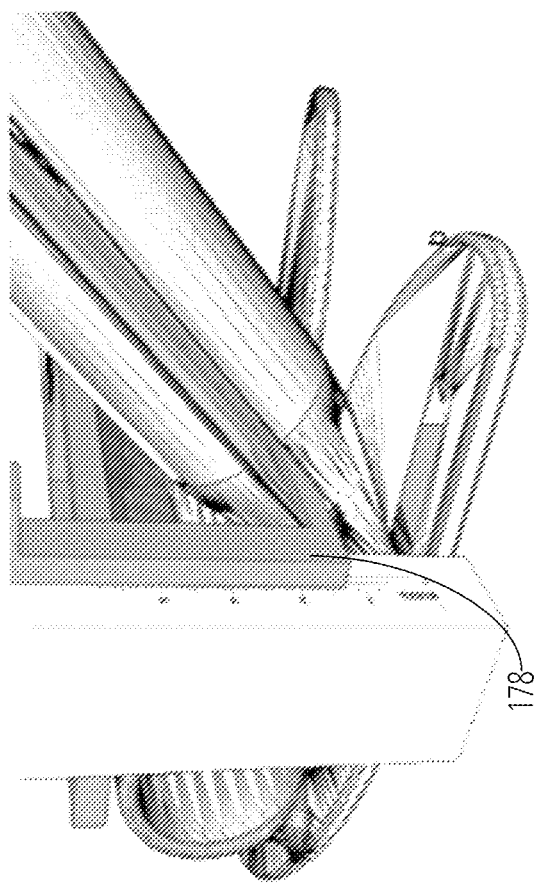

FIGS. 21A and 21B are views of an example embodiment of an apparatus that can be used to insert a needle, catheter, and so forth into a patient. The apparatus of FIGS. 21A and 21B can include a needle holder 168, a plunger 170, a needle/plunger lock 172, a fixed door portion 174, a movable door portion 176, and an angle adjuster 178. The angle adjuster 178 can, in contrast to the angle adjustment knob 110, be configured to adjust the angle of the swing arm 104 by traveling linearly. In some embodiments, the swing arm 104 can contain electronics similar to the electronics discussed above, or the apparatus of FIGS. 21A and 21B can operate without electronics.

FIGS. 22A-G show views of an apparatus having a fixed door portion 174 and movable door portion 176 during various stages of a procedure for inserting a needle into a patient. With this mechanism, all needles can start at the same angle and distance, which can reduce or eliminate the need to measure the needle length.

Figure 22A:
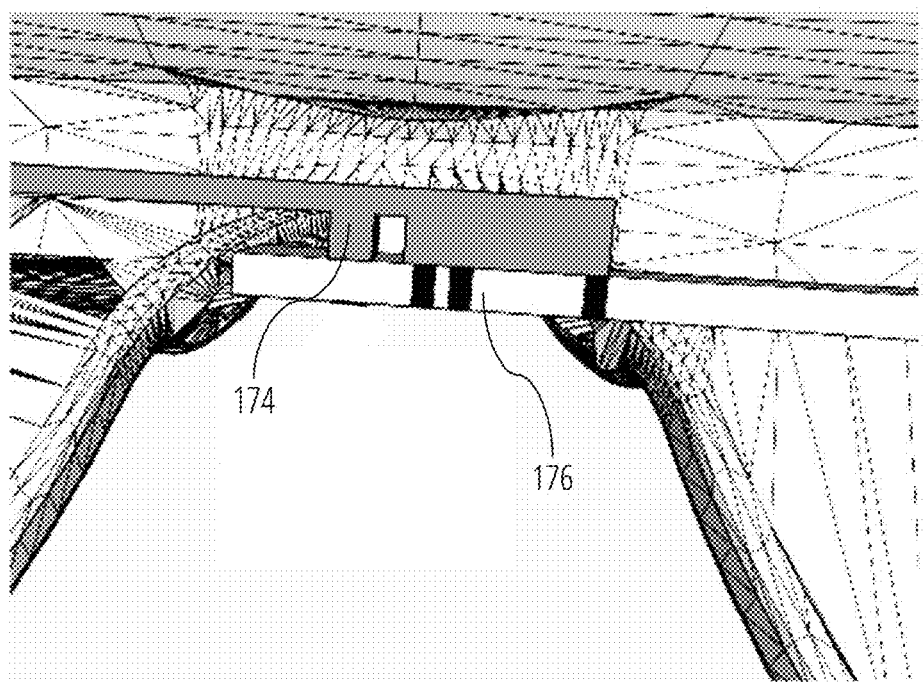
FIGS. 22A-G are views that illustrate a needle insertion process according to some embodiments.
Figure 22B:
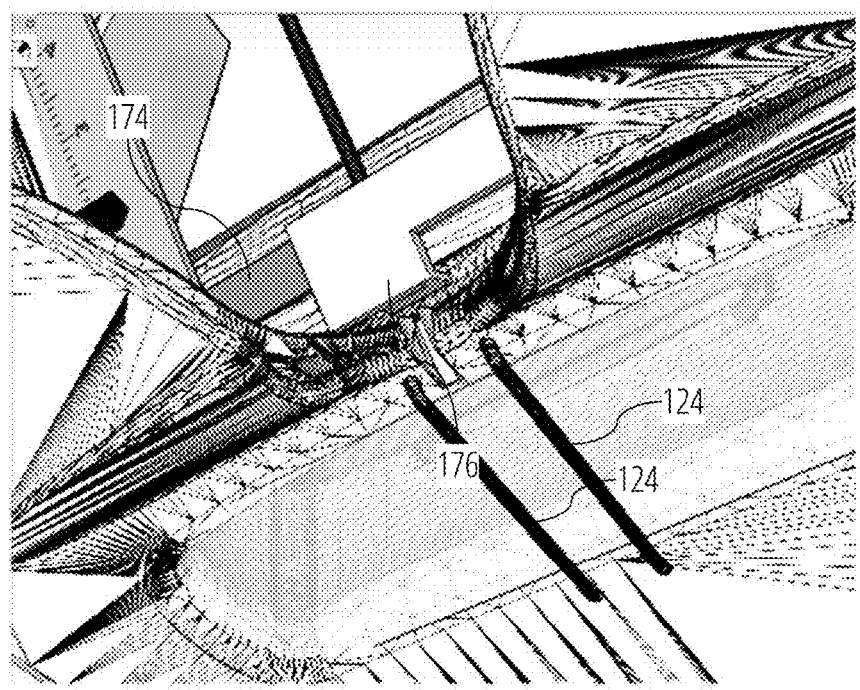

As shown in FIGS. 22A and 22B, the apparatus can have a fixed door portion 174 and a movable door portion 176. The movable door portion 176 can be initially positioned to prevent a needle from traveling forward or downed (i.e., from moving toward the patient). Thus, in a closed configuration, the movable door portion 176 can prevent the needle from puncturing the patient's skin. For example, the movable door portion 176 can be positioned as indicated in FIGS. 22A and 22B when the provider is scanning for a target vein using an ultrasound probe.

Figure 22C:
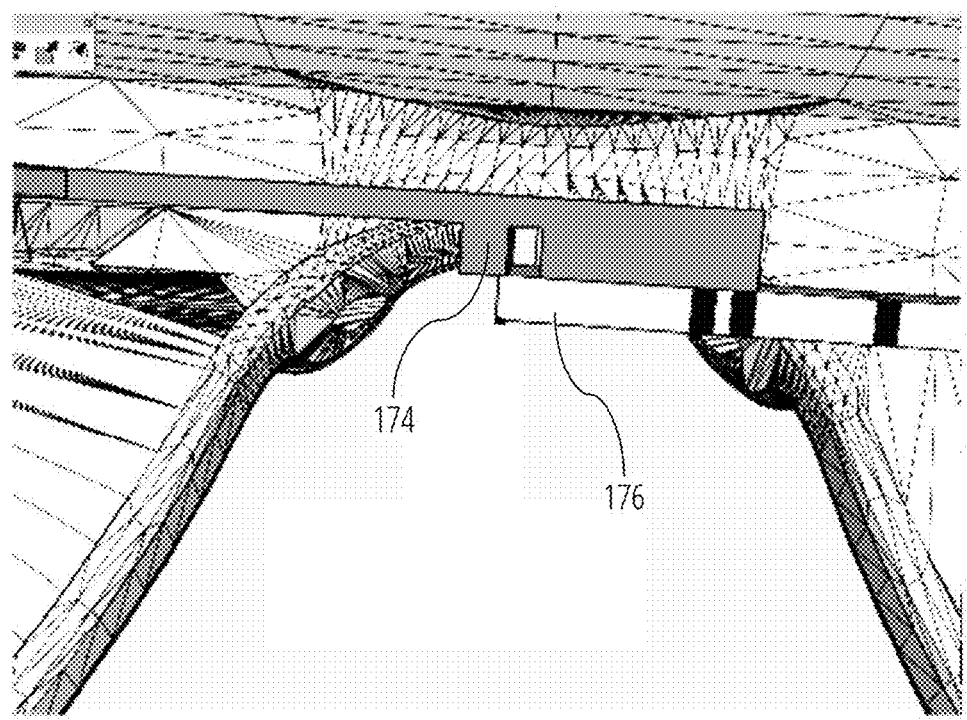
Figure 22D:
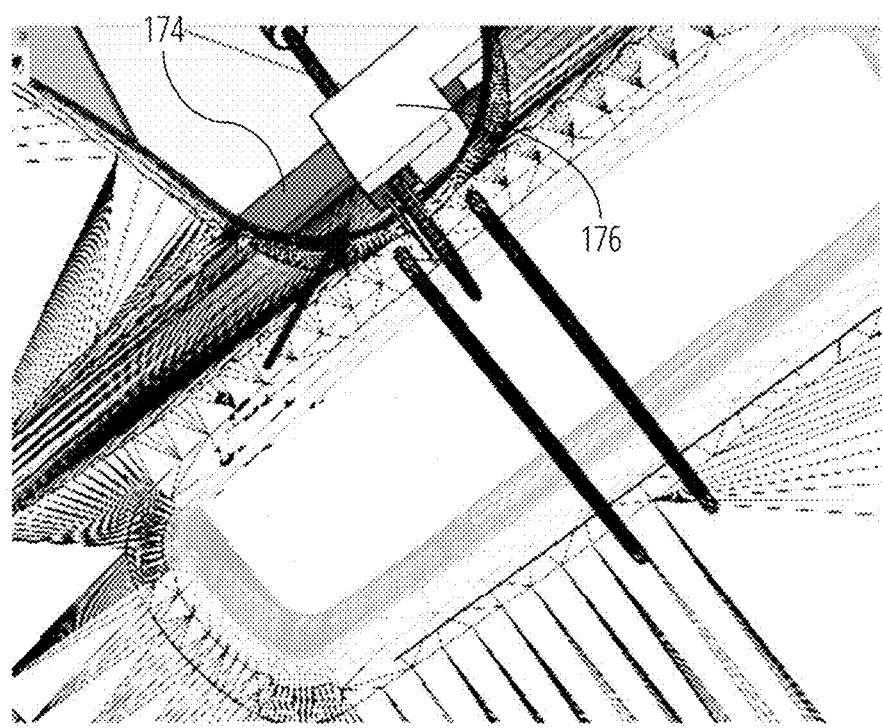

After locating a target vein, the provider can move the movable door portion 176 into a second position as shown in FIGS. 22C and 22D. In the second position, the needle may password forward toward the patient, for example as a result of the provider pushing on the plunger 170, but the path of the needle can be constrained because the fixed door portion 174 and movable door portion 176 form a hole that confines the needle to substantially linear movement. The needle may have a small degree of flexibility in pose and direction, for example because the opening created by the fixed door portion 174 and movable door portion 176 may be somewhat larger than the outer diameter of the needle.

Figure 22E:
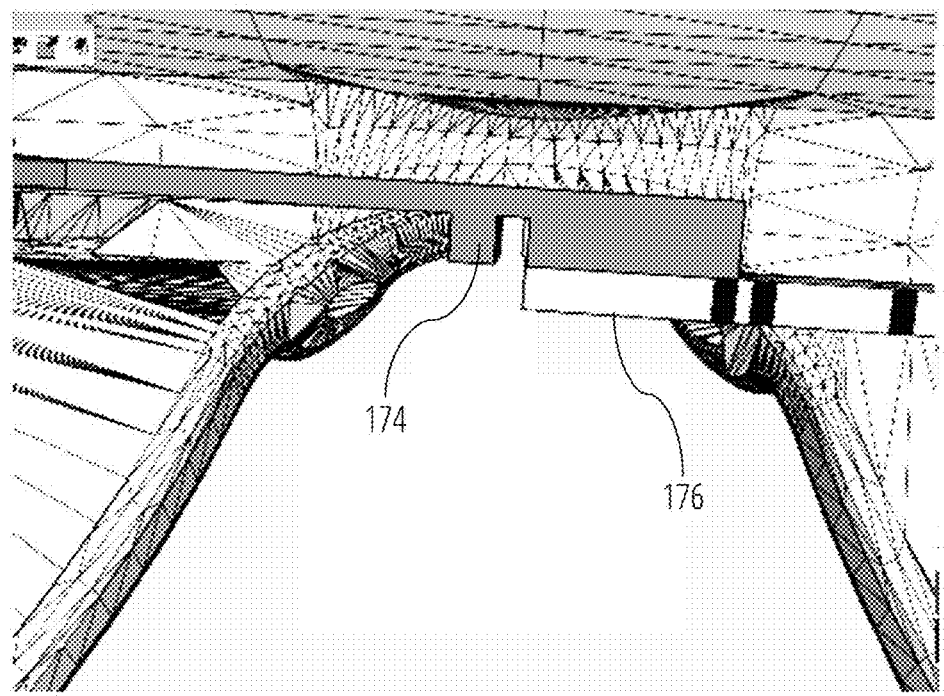
Figure 22F:
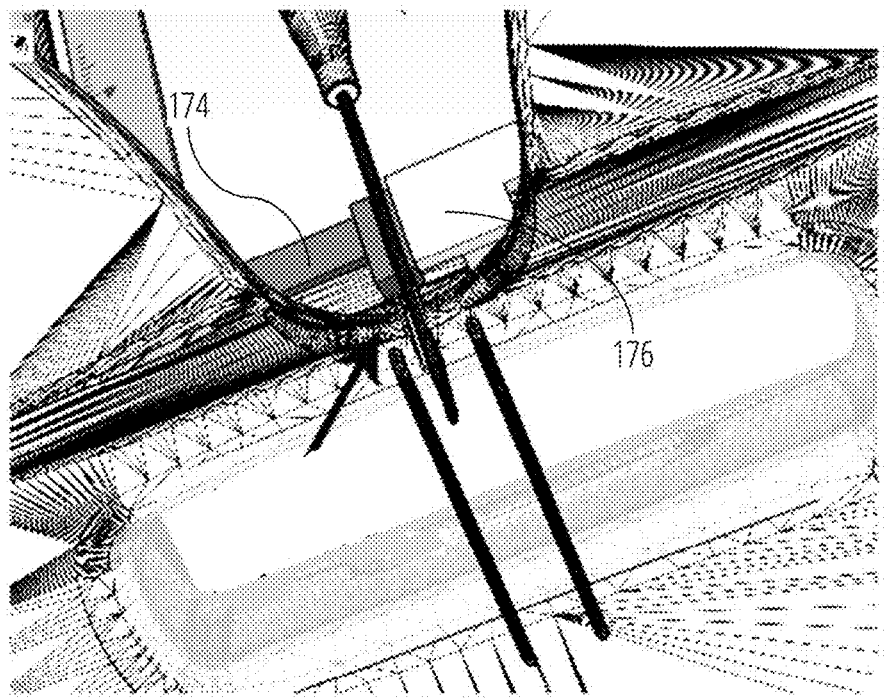
Figure 22G:
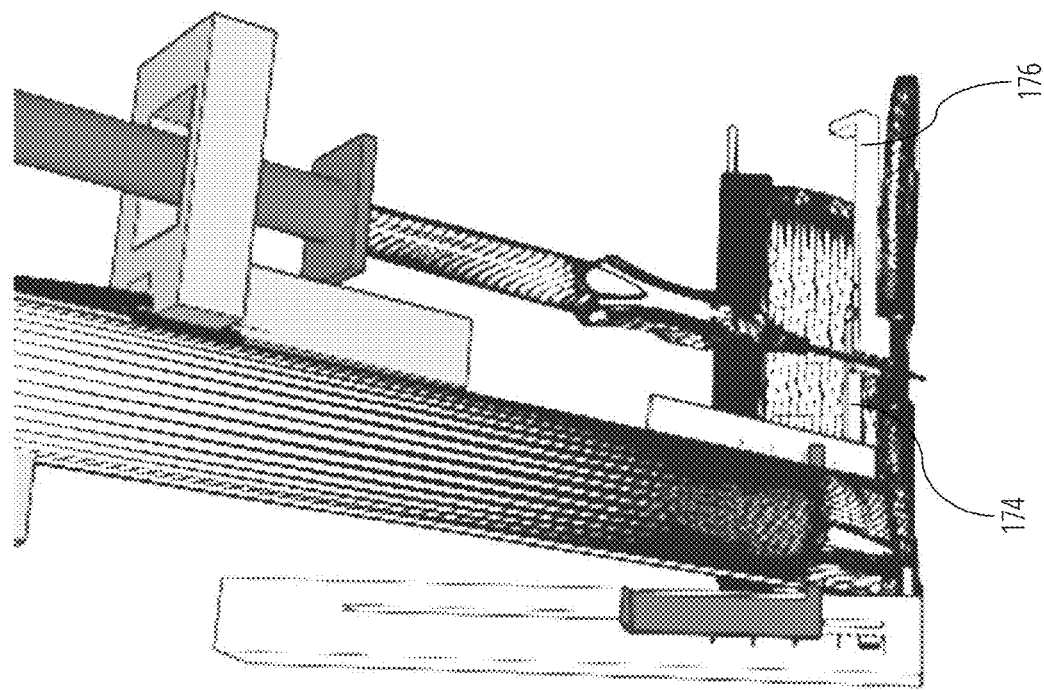

Once the needle is inserted into the patient to the desired depth, the movable door portion 176 can be moved to a third position as shown in FIGS. 22E and 22F. In this configuration, the angle of the needle can be freely decreased with respect to the patient's skin surface. For example, a provider may reduce the angle in preparation for feeding a catheter. FIG. 22G shows another view of the apparatus when the movable door portion 176 is in the third position.

Figure 23A:
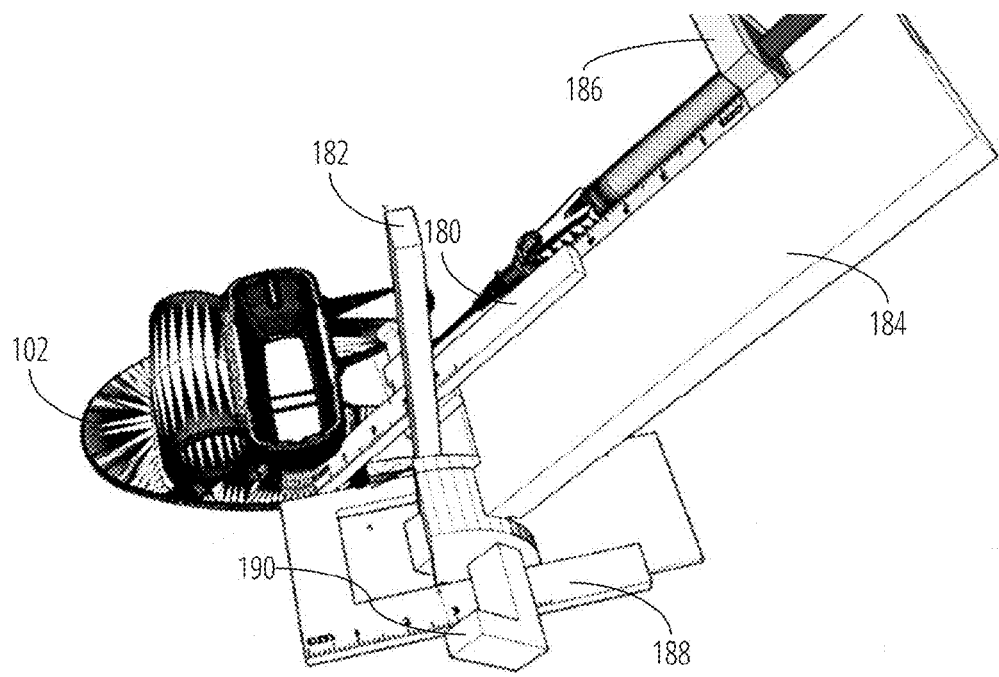
FIGS. 23A-D are views of an example embodiment of an insertion apparatus.
Figure 23B:
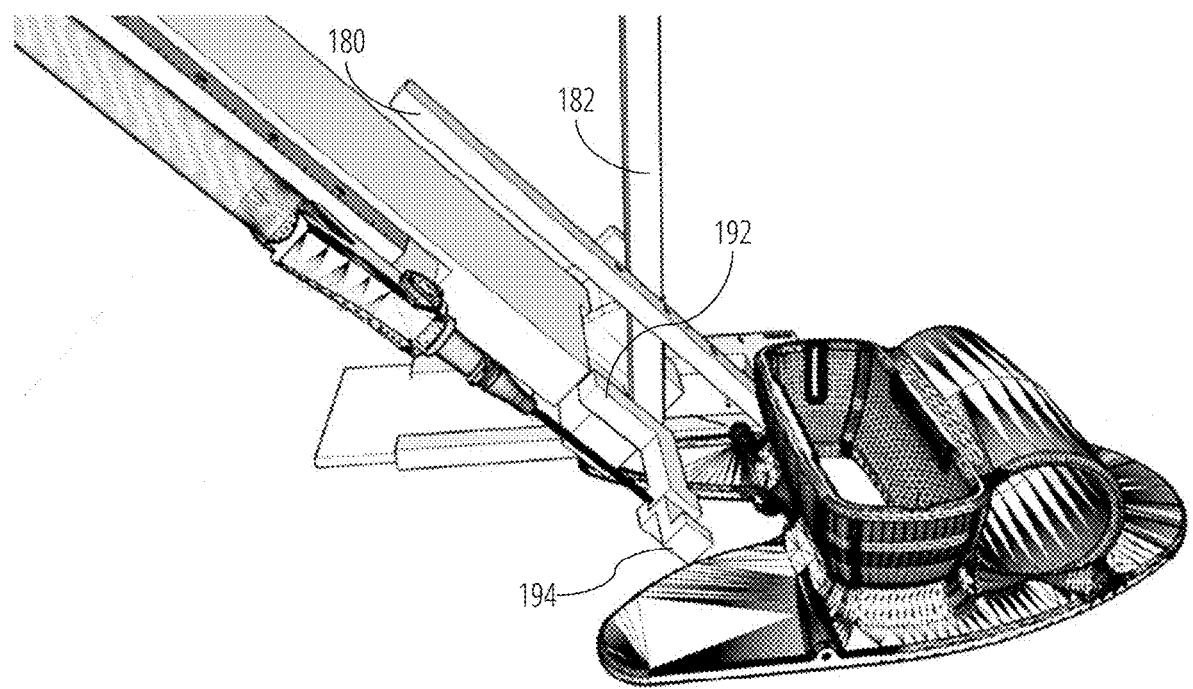
Figure 23D:
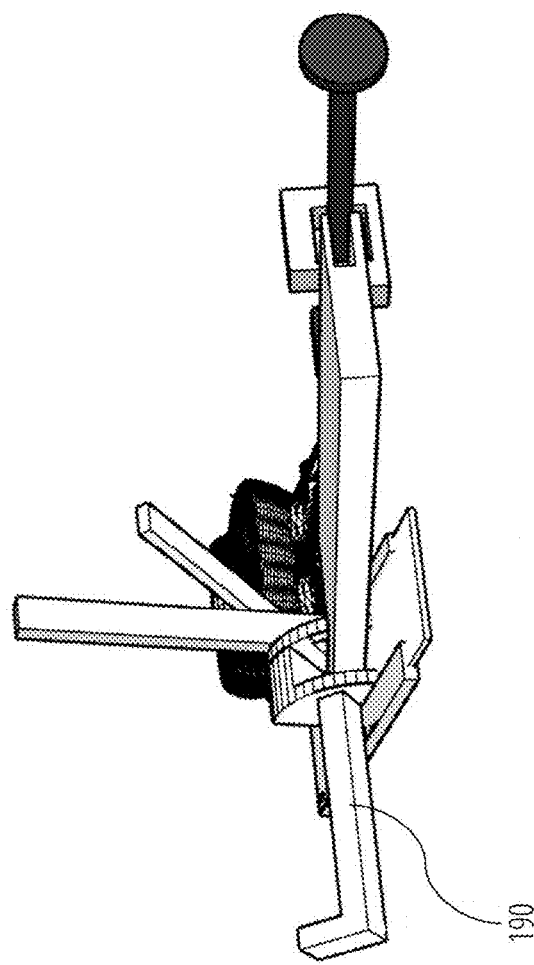
Figure 23C:
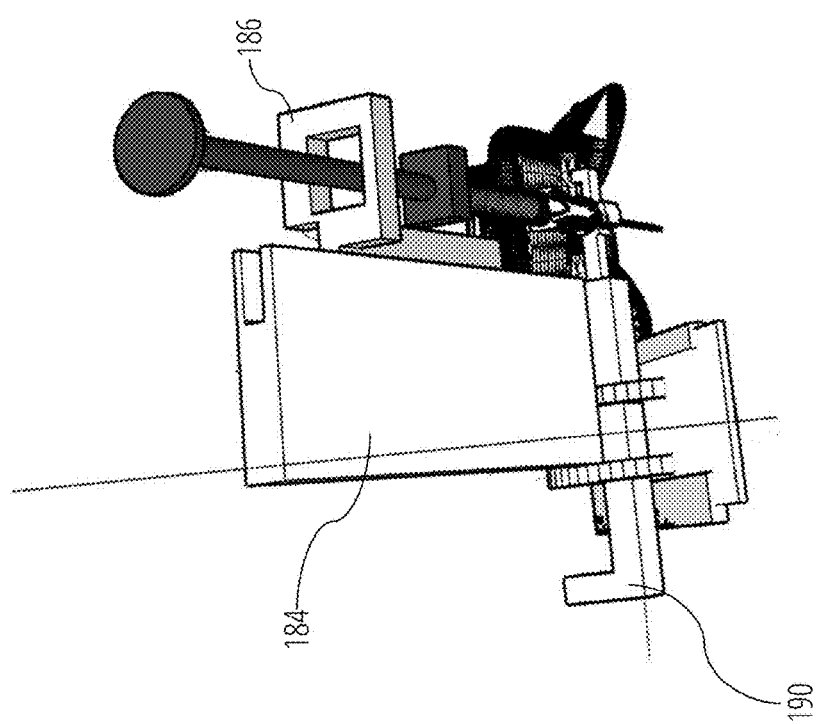

FIGS. 23A-22D show another example embodiment of an apparatus for guided insertion of a needle, catheter, and so forth. The apparatus can include a base 102, a reference ruler 180 that is immovably fixed to the base at a predetermined angle, a measurement post 182, a ramp 184, a needle/plunger holder 186, a positioning guide 188, a release peg 190, a fixed door portion 192, and a movable door portion 194.

The ramp 184 can slide inside the positioning guide 188, which can have markings to indicate the distance of the needle tip from the ultrasound probe. The measurement post 182 can be attached to and move with the ramp 184. The measurement post 182 can be used in conjunction with the reference ruler 180. The distance markings on the device can be used to determine how far to push the needle to achieve a desired insertion depth when the needle is below (e.g., directly below) the ultrasound probe.

The apparatus shown in FIGS. 23A-D can be configured so that the ramp 184 is set to a predetermined angle. When the release peg 190 is removed or pulled from under the ramp 184, the ramp 184 may freely fall, thereby enabling the provider to adjust the angle of the needle.

Figure 24A:
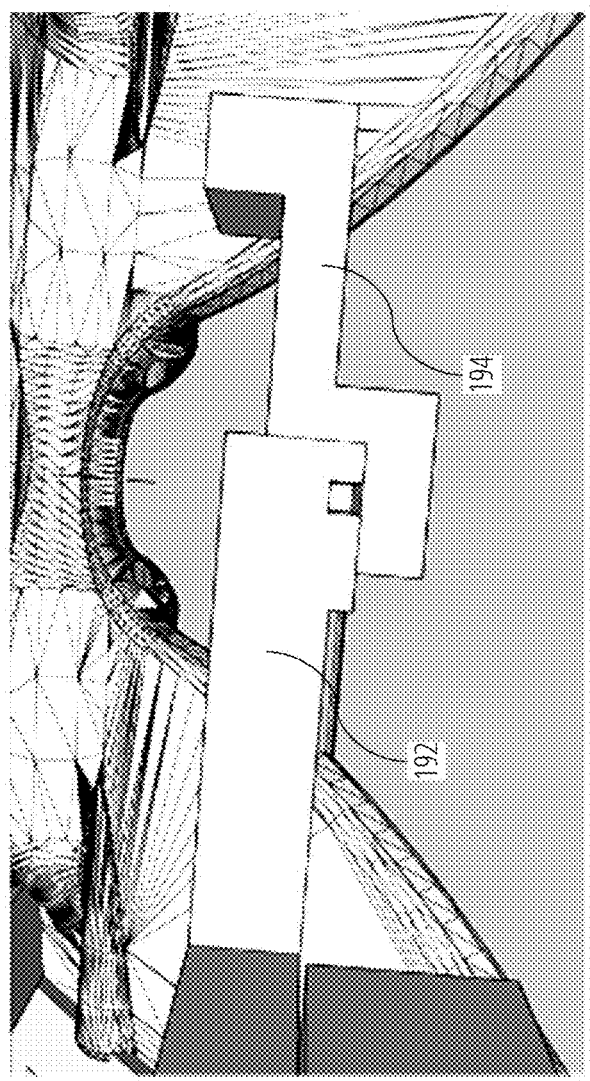
FIGS. 24A-E are views that illustrate a needle insertion process according to some embodiments.
Figure 24C:
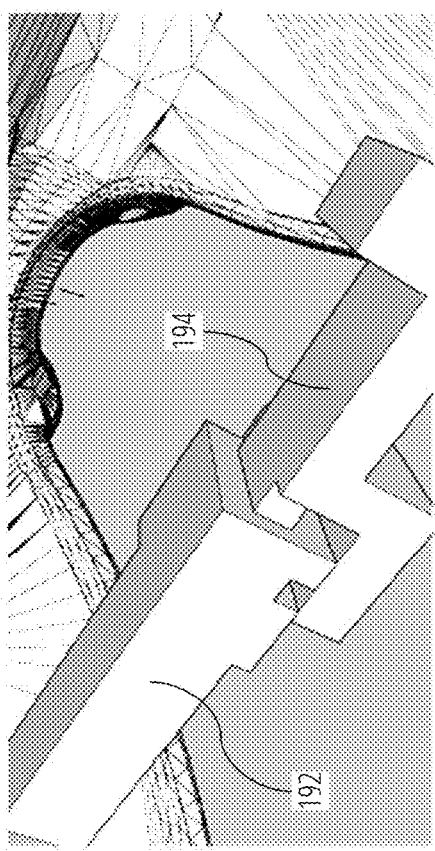
Figure 24B:
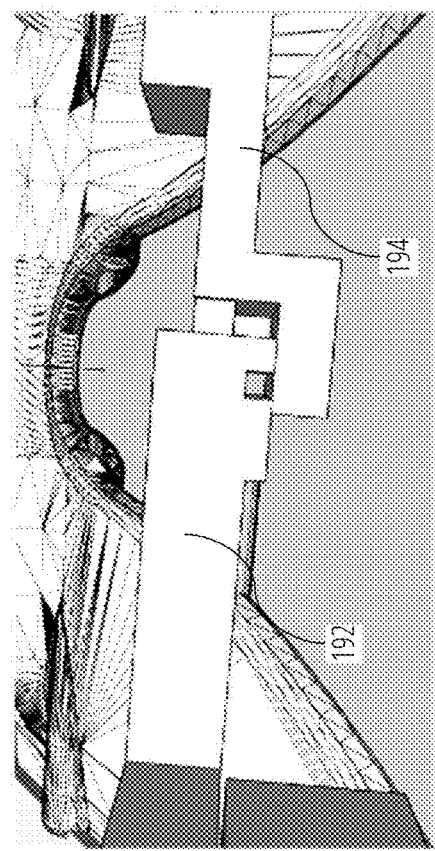
Figure 24D:
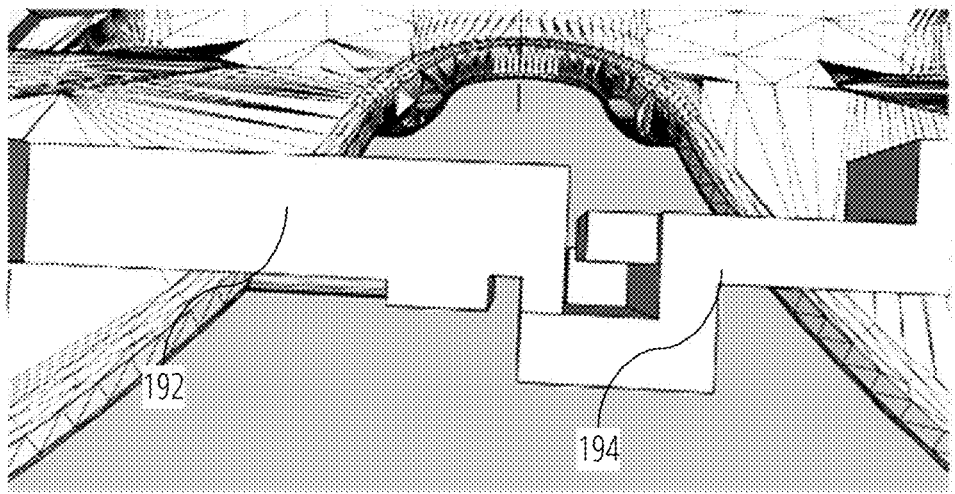
Figure 24E:
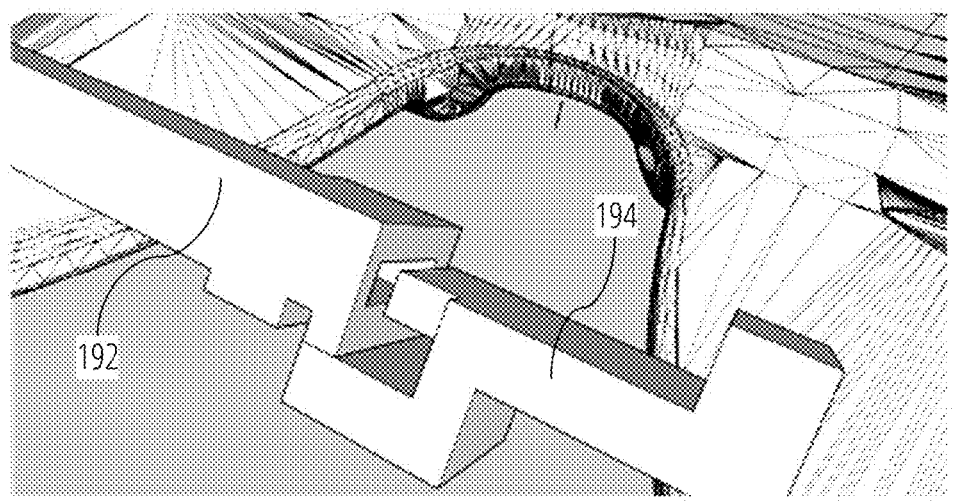
Figure 25A:
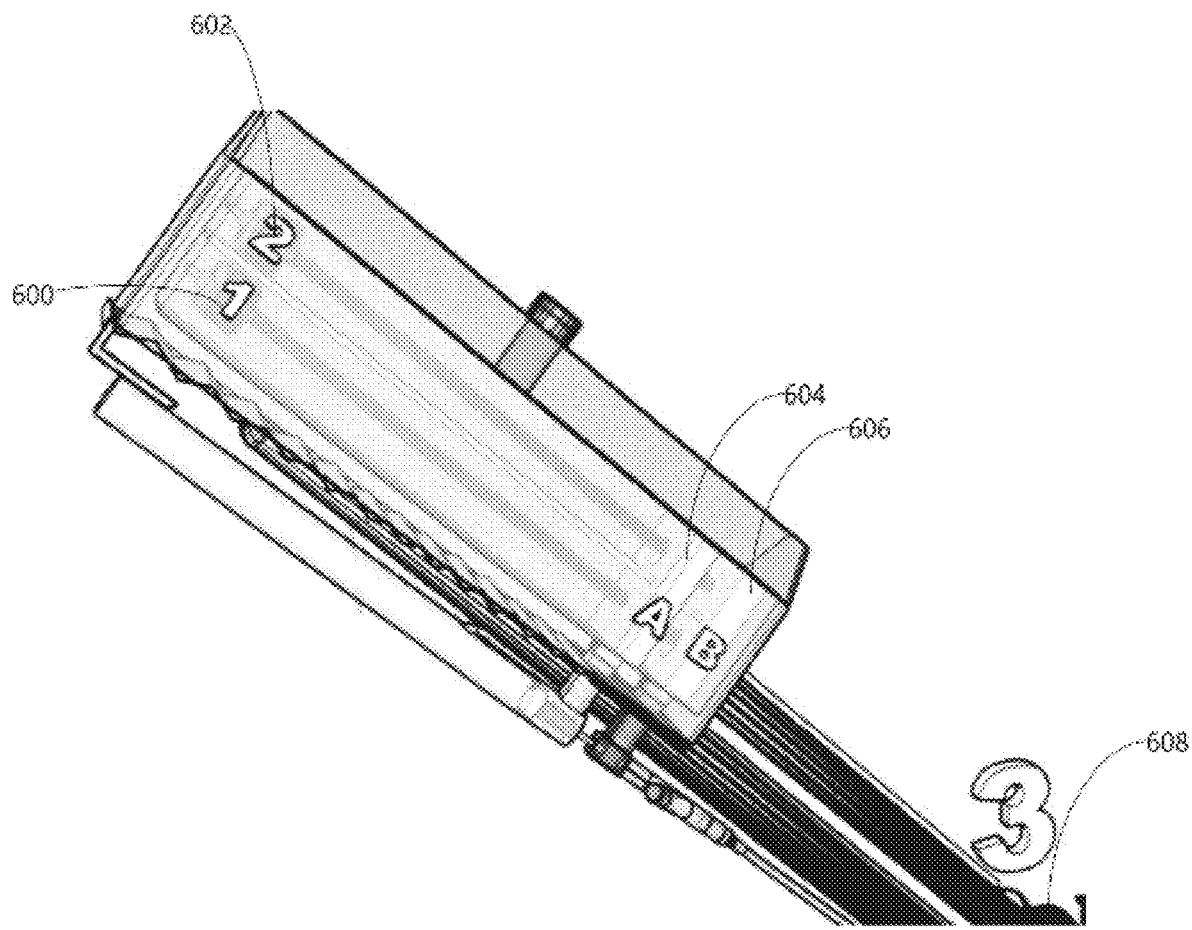
FIGS. 25A-D are views of an apparatus for automated needle insertion according to some embodiments.
Figure 25B:
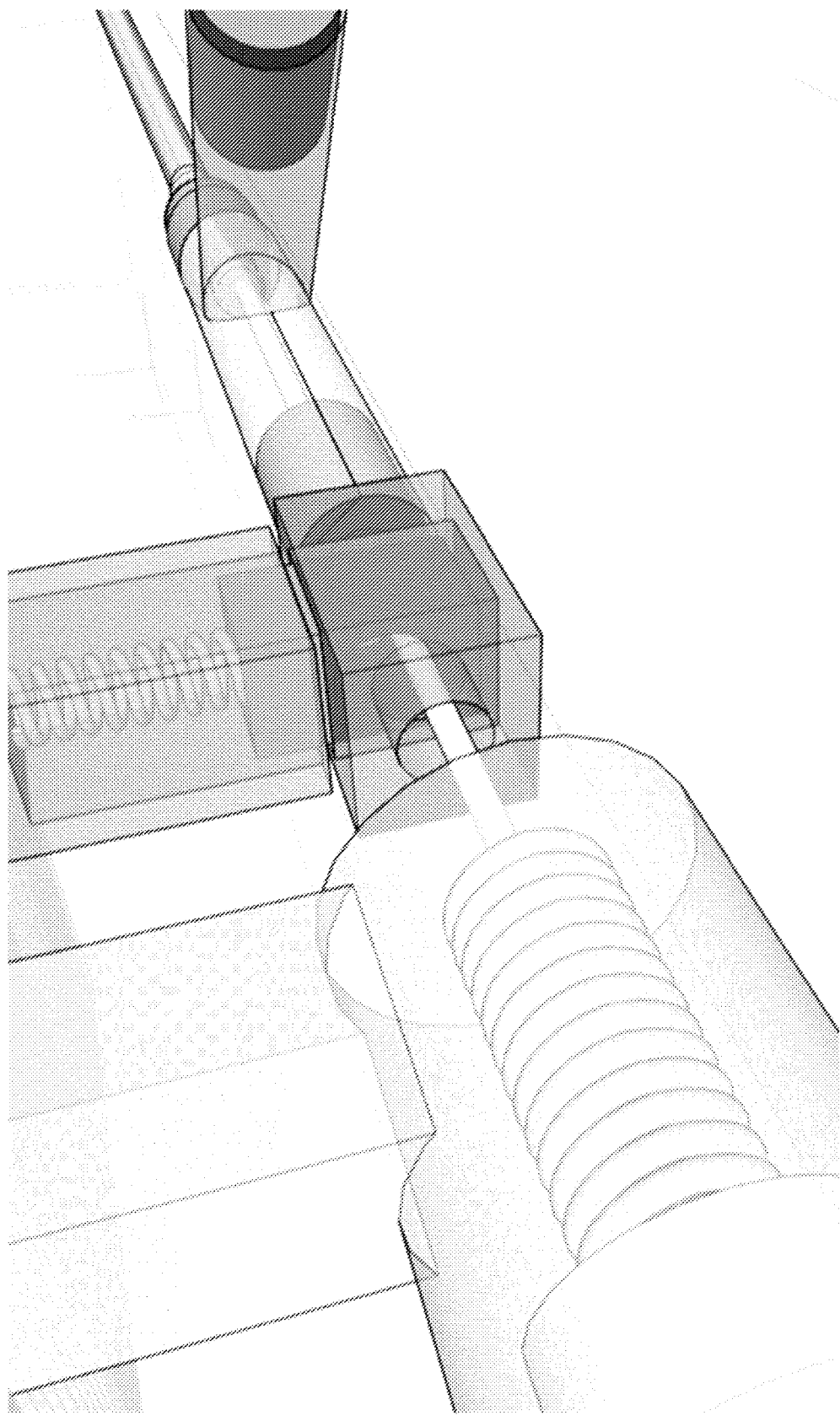
Figure 25C:
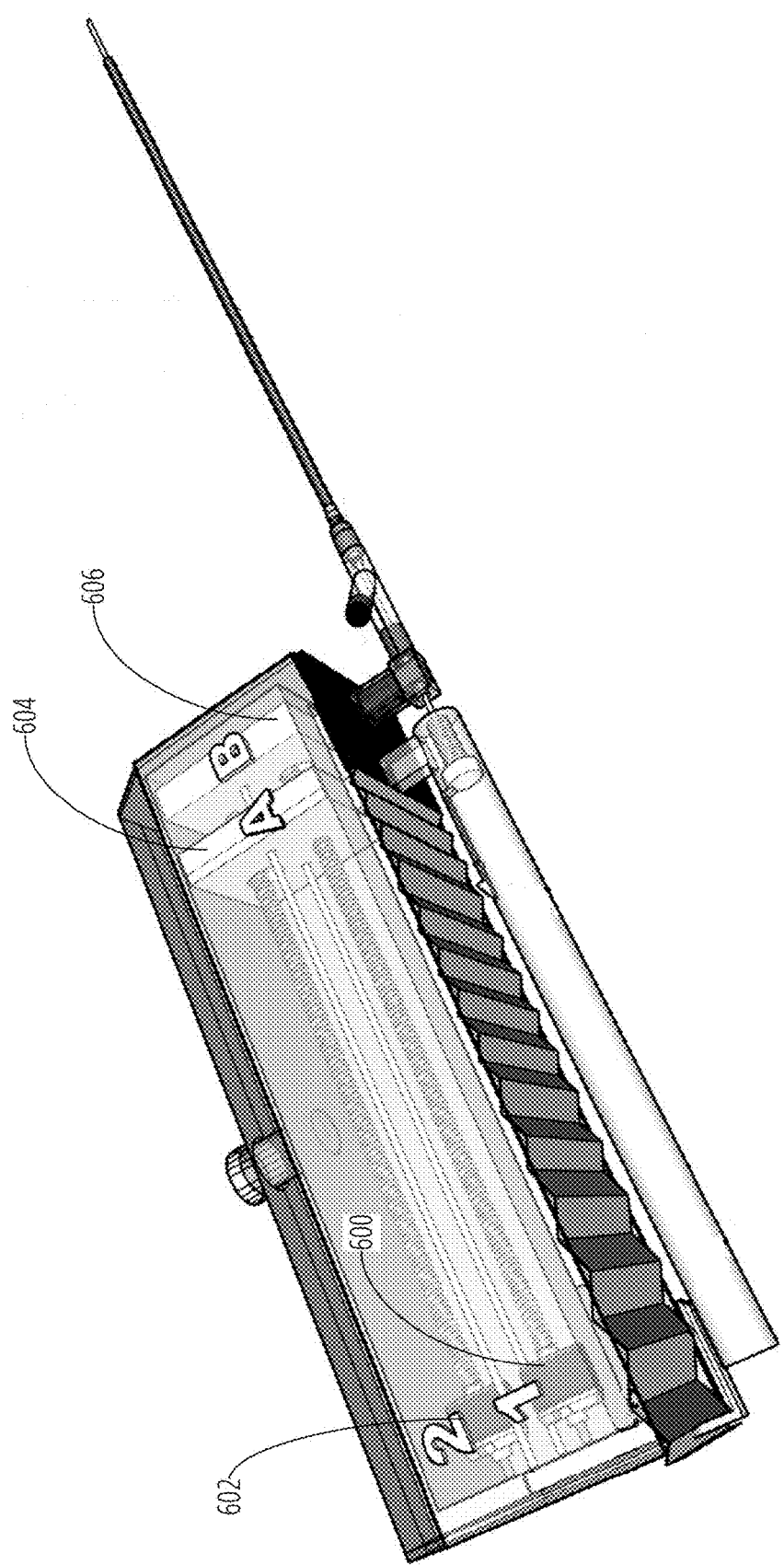
Figure 25D:
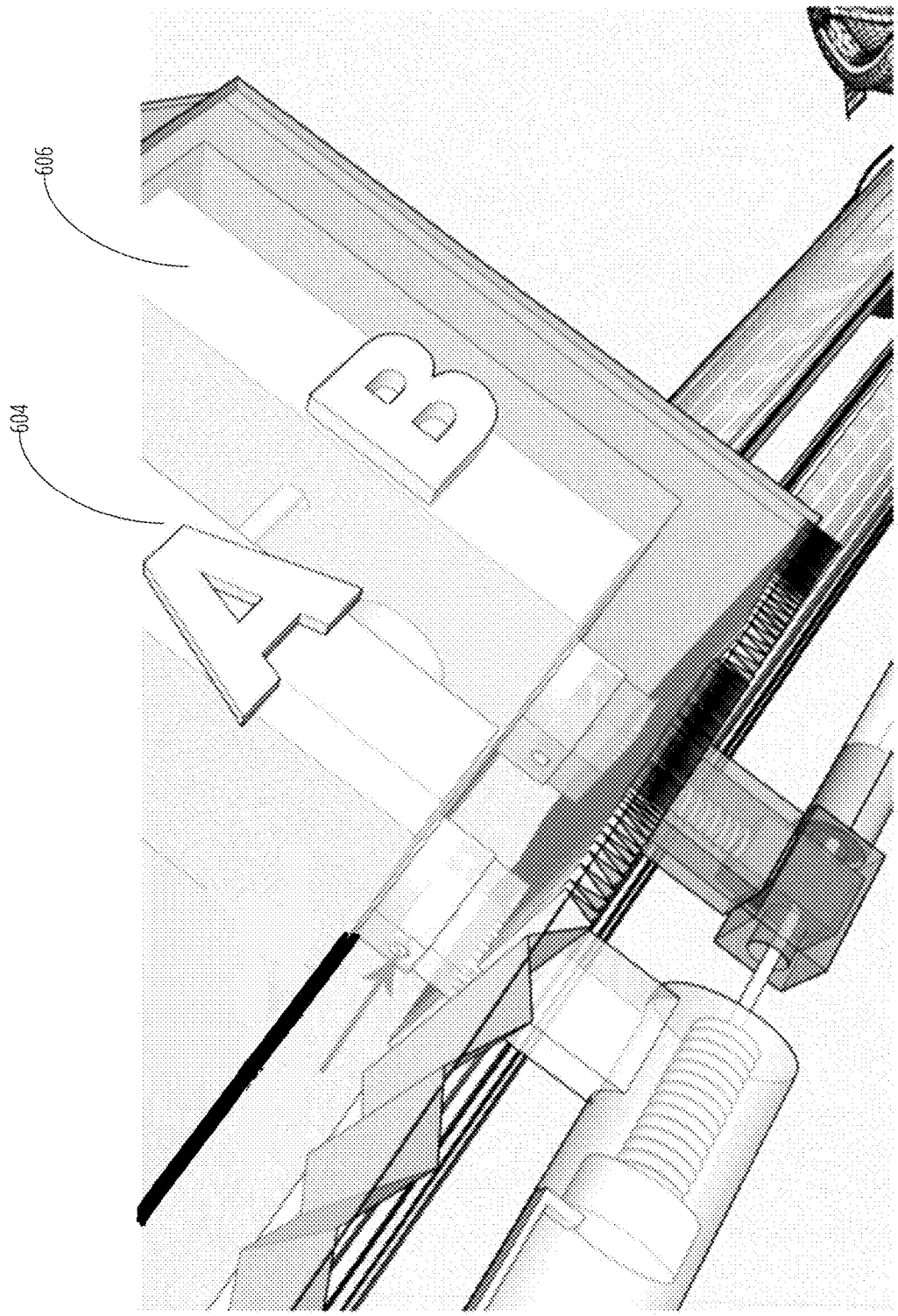

FIGS. 24A-E illustrate an embodiment of a fixed door portion 192 and movable door portion 194 that operates similarly to the fixed door portion 174 and movable door portion 176 illustrated in FIGS. 22A-G. In FIG. 24A, the movable door portion 194 is positioned such that a needle cannot pass. In FIGS. 24B and 24C, the movable door portion 194 is positioned such that there is an opening formed by the fixed door portion 192 and movable door portion 194, allowing a needle to advance forward toward the patient's skin while substantially restricting movement in other directions and substantially limiting changes in the pose of the needle. FIGS. 24D and 24E illustrate a third position of the movable door portion 194 with respect to the fixed door portion 192, wherein the channel formed by the fixed door portion 192 and movable door portion 194 is open, allowing the needle angle to be decreased with respect to the patient's skin.

Automated Insertion

The apparatuses described above can automate some steps and/or can assist the user in inserting a needle to a desired location inside a patient. However, the embodiments described above still require that the user insert the needle manually. While this approach offers flexibility to the user, for example, the user can make small alterations if warranted, such as if the user observes some movement on the ultrasound display. However, this approach can also lead to errors, such as not pushing the need in far enough or pushing the needle too far. Accordingly, in some embodiments it can be advantageous to automatic the needle insertion.

FIGS. 25A-D show example embodiments of part of an apparatus that can be used for automated needle insertion. In some embodiments, the first motor 600 (labeled 1) can be mechanically coupled to and control the movement of the first plate 604 (labeled A). In some embodiments, an apparatus can include a second motor 602 (labeled 2) that can be mechanically coupled to and control the movement of the second plate 606 (labeled B). In some embodiments, a third motor 608 (labeled 3) can be used to control an insertion angle of a needle. The apparatus shown in FIGS. 25A-D can be, for example, adapted to an apparatus that is similar to the apparatus 100, or can be adapted to another embodiment of an insertion apparatus. Some embodiments can include a sensor, such as an optical sensor, that can detect the presence of blood in a transparent or partially transparent portion of a catheter.

As an example, when inserting a catheter (e.g., a needle surrounded by a catheter sheath), the first motor 600 and second motor 602 can move together to drive the second motor 602 and second plate 606 to drive the needle and catheter tubing forward, an optical sensor, which can be disposed near the distal end of the apparatus, can detect blood, and a processor can be configured to cause the third motor 608 to decrease the angle of the needle. The first motor 600 and first plate 604 can then drive the needle further into the patient. The first motor 600 can drive the second motor 602 backwards, away from the patient, to extract the needle, leaving the second plate 606 in place and holding the catheter. In some cases, the needle and catheter can also include a protective housing. The protective housing can include a lever or push button that, when depressed, causes the needle to retract into the protective housing. In some embodiments, the lever can be depressed automatically as the first motor 600 retracts the needle.

Computing Systems

Figure 26:
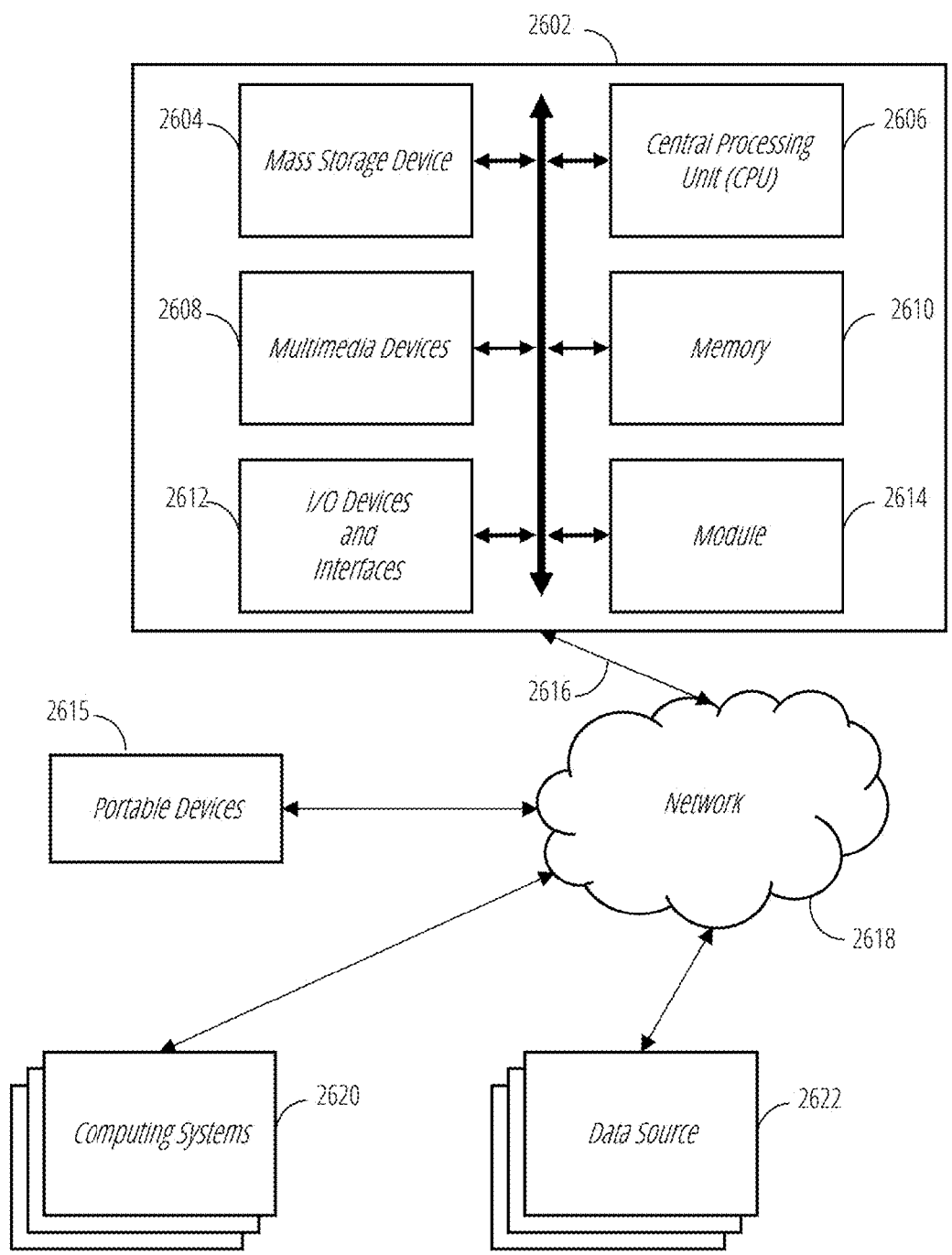
FIG. 26 is a block diagram of an embodiment of a computing device that can be used for performing some of the methods and processes described herein.

FIG. 26 is a block diagram depicting an embodiment of a computer hardware system configured to run software for implementing one or more embodiments disclosed herein.

In some embodiments, the systems, processes, and methods described herein are implemented using a computing system, such as the one illustrated in FIG. 26. The example computer system 2602 is in communication with one or more computing systems 2620 and/or one or more data sources 2622 via one or more networks 2618. While FIG. 26 illustrates an embodiment of a computing system 2602, it is recognized that the functionality provided for in the components and modules of computer system 2602 may be combined into fewer components and modules, or further separated into additional components and modules.

The computer system 2602 can comprise a module 2614 that carries out the functions, methods, acts, and/or processes described herein. The module 2614 is executed on the computer system 2602 by a central processing unit 2606 discussed further below.

In general, the word "module," as used herein, refers to logic embodied in hardware or firmware or to a collection of software instructions, having entry and exit points. Modules are written in a program language, such as JAVA, C or C++, Python, or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 2602 includes one or more processing units (CPU) 2606, which may comprise a microprocessor. The computer system 2602 further includes a physical memory 2610, such as random-access memory (RAM) for temporary storage of information, a read only memory (ROM) for permanent storage of information, and a mass storage device 2604, such as a backing store, hard drive, rotating magnetic disks, solid state disks (SSD), flash memory, phase-change memory (PCM), diskette, or optical media storage device. Alternatively, the mass storage device may be implemented in an array of servers. Typically, the components of the computer system 2602 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 2602 includes one or more input/output (I/O) devices and interfaces 2612, such as a keyboard, mouse, touch pad, and printer. The I/O devices and interfaces 2612 can include one or more display devices, such as a monitor, that allows the visual presentation of data to a user. More particularly, a display device provides for the presentation of GUIs as application software data, and multi-media presentations, for example. The I/O devices and interfaces 2612 can also provide a communications interface to various external devices. The computer system 2602 may comprise one or more multi-media devices 2608, such as speakers, video cards, graphics accelerators, and microphones, for example.

The computer system 2602 may run on a variety of computing devices, such as a server, a Structure Query Language server, a personal computer, a laptop computer, and so forth. In other embodiments, the computer system 2602 may run on a cluster computer system, a mainframe computer system and/or other computing system suitable for controlling and/or communicating with large databases, performing high volume transaction processing, and generating reports from large databases. The computing system 2602 is generally controlled and coordinated by an operating system software, including proprietary operating systems. Operating systems control and schedule computer processes for execution, perform memory management, provide file system, networking, and I/O services, and provide a user interface, such as a graphical user interface (GUI), among other things.

The computer system 2602 illustrated in FIG. 26 is coupled to a network 2618, such as a LAN, WAN, or the Internet via a communication link 2616 (wired, wireless, or a combination thereof). Network 2618 communicates with various computing devices and/or other electronic devices, such as, for example, portable devices 2615. Network 2618 is communicating with one or more computing systems 2620 and one or more data sources 2622. The module 2614 may access or may be accessed by computing systems 2620 and/or data sources 2622 through a web-enabled user access point. Connections may be a direct physical connection, a virtual connection, and other connection type. The web-enabled user access point may comprise a browser module that uses text, graphics, audio, video, and other media to present data and to allow interaction with data via the network 2618.

Access to the module 2614 of the computer system 2602 by computing systems 2620 and/or by data sources 2622 may be through a web-enabled user access point such as the computing systems' 2620 or data source's 2622 personal computer, cellular phone, smartphone, laptop, tablet computer, e-reader device, audio player, or another device capable of connecting to the network 2618. Such a device may have a browser module that is implemented as a module that uses text, graphics, audio, video, and other media to present data and to allow interaction with data via the network 2618.

The output module may be implemented as a combination of an all-points addressable display such as a cathode ray tube (CRT), a liquid crystal display (LCD), a plasma display, or other types and/or combinations of displays. The output module may be implemented to communicate with input devices 2612 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 2602 may comprise a physical or logical connection established between a remote microprocessor and a mainframe host computer for the express purpose of uploading, downloading, or viewing interactive data and databases on-line in real time. The remote microprocessor may be operated by an entity operating the computer system 2602, including the client server systems or the main server system, an/or may be operated by one or more of the data sources 2622 and/or one or more of the computing systems 2620. In some embodiments, terminal emulation software may be used on the microprocessor for participating in the micro-mainframe link.

In some embodiments, computing systems 2620 who are internal to an entity operating the computer system 2602 may access the module 2614 internally as an application or process run by the CPU 2606.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer.

This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 2602 may include one or more internal and/or external data sources (for example, data sources 2622). In some embodiments, one or more of the data repositories and the data sources described above may be implemented using a relational database as well as other types of databases such as, for example, a NoSQL database, a flat file database, an entity-relationship database, an object-oriented database, a cloud-based database, a non-relational database, or a record-based database.

The computer system 2602 may also access one or more databases 2622. The databases 2622 may be stored in a database or data repository. The computer system 2602 may access the one or more databases 2622 through a network 2618 or may directly access the database or data repository through I/O devices and interfaces 2612. The data repository storing the one or more databases 2622 may reside within the computer system 2602.

Additional Embodiments

In the foregoing specification, the systems and processes have been described with reference to specific embodiments thereof. It will, however, be evident that various modifications and changes may be made thereto without departing from the broader spirit and scope of the embodiments disclosed herein. The specification and drawings are, accordingly, to be regarded in an illustrative rather than restrictive sense.

Indeed, although the systems and processes have been disclosed in the context of certain embodiments and examples, it will be understood by those skilled in the art that the various embodiments of the systems and processes extend beyond the specifically disclosed embodiments to other alternative embodiments and/or uses of the systems and processes and obvious modifications and equivalents thereof. In addition, while several variations of the embodiments of the systems and processes have been shown and described in detail, other modifications, which are within the scope of this disclosure, will be readily apparent to those of skill in the art based upon this disclosure. It is also contemplated that various combinations or sub-combinations of the specific features and aspects of the embodiments may be made and still fall within the scope of the disclosure. It should be understood that various features and aspects of the disclosed embodiments can be combined with, or substituted for, one another in order to form varying modes of the embodiments of the disclosed systems and processes. Any methods disclosed herein need not be performed in the order recited. Thus, it is intended that the scope of the systems and processes herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and sub-combinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable sub-combination. Moreover, although features may be described above as acting in certain combinations and even initially claimed as such, one or more features from a claimed combination may in some cases be excised from the combination, and the claimed combination may be directed to a sub-combination or variation of a sub-combination. No single feature or group of features is necessary or indispensable to each and every embodiment.

It will also be appreciated that conditional language used herein, such as, among others, "can," "could," "might," "may," "for example," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the embodiments are not to be limited to the particular forms or methods disclosed, but, to the contrary, the embodiments are to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (for example, as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (for example, as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein but are to be accorded the widest scope consistent with this disclosure, the principles and the novel features disclosed herein.

What is claimed is:

1. An apparatus for inserting a needle into a patient, the apparatus comprising:
a base, the base having a cavity for receiving an ultrasound probe;
a finger receiver on the base, the finger receiver configured to allow a user to insert a finger into the finger receiver, and the finger receiver configured to allow the user to position the apparatus with the finger;
a swing arm pivotably coupled to the base at a pivot point, the pivot point located at a distal end of the swing arm and the swing arm extending proximally from the pivot point along an axis;
a printed circuit board (PCB) board positioned inside the swing arm and extending parallel to the axis;
a first linear position sensing track mounted on the PCB board and extending parallel to the axis comprising a first plurality of active electrodes;
a second linear position sensing track mounted on the PCB board and extending parallel to the axis comprising a second plurality of active electrodes;
an angle sensor disposed about the pivot point;
a needle guide slidably mounted to the first linear position sensing track configured to move along the first linear position sensing track comprising a first plurality of passive electrodes;
an insertion depth slider slidably mounted to the second linear position sensing track configured to move along the second linear position sensing track comprising a second plurality of passive electrodes;
a power source;
a non-transitory computer readable storage medium having program instructions embodied therewith; and
one or more processors configured to execute the program instructions to cause the apparatus to:
prompt the user to measure a length of the needle;
determine, using the first linear position sensing track and the needle guide, the length of the needle by measuring capacitance with the first plurality of active electrodes and the first plurality of passive electrodes to determine the linear position of the needle guide;
prompt the user to set a target insertion depth for the needle;
adjust, using the second linear position sensing track and the insertion depth slider, the target insertion depth of the needle by measuring capacitance with the second plurality of active electrodes and the second plurality of passive electrodes to determine the linear position of the insertion depth slider;
determine, using the angle sensor, an insertion angle, wherein the insertion angle is an angle of the swing arm with respect to the base;
prompt the user to insert the needle into the patient;
based at least in part on the needle length and the insertion angle, determine that the user has inserted the needle to the target insertion depth; and
provide a first indication to the user that the needle has been inserted to the target insertion depth.

2. The apparatus of claim 1, wherein a bottom surface of the base is curved.

3. The apparatus of claim 1, wherein a bottom surface of the base is flat.

4. The apparatus of claim 1, wherein the computer-readable storage medium further includes instructions that, when executed by the one or more processors, cause the apparatus to:
compare the angle of the swing arm to a target angle; and
provide a second indication to the user when the angle of the swing arm is within a threshold angle of the target angle.

5. The apparatus of claim 4, wherein the threshold angle is about 1 degree.

6. The apparatus of claim 1, further comprising a display.

7. The apparatus of claim 6, wherein the computer-readable storage medium further includes instructions that, when executed by the one or more processors, cause the apparatus to:
- after prompting the user to set the needle length, display a current needle length;
- after prompting the user to set the target insertion depth, display a current insertion depth; and
- after prompting the user to set the insertion angle, display a current insertion angle,
- wherein the current needle length changes as the user moves the needle guide along the first linear position sensing track,
- wherein the current insertion depth changes as the user moves the insertion depth slider along the second linear position sensing track, and
- wherein the current insertion angle changes as the user adjusts the angle of the swing arm.

8. The apparatus of claim 1, further comprising at least one guide bar, wherein the at least one guide bar is positioned in a sensing path of the ultrasound probe.

9. The apparatus of claim 1, wherein the first indication, a second indication and a third indication comprise any combination of one or more of illuminating a light-emitting diode, altering content of a display, and playing a sound.

10. The apparatus of claim 1, further comprising:
- a needle measurement hole disposed at a proximal end of the swing arm configured to receive the needle; and
- a hilt sensor located at the needle measurement hole and configured to be activated by a hilt of the needle,
- wherein determining the length of the needle comprises:
  - inserting the needle into the needle measurement hole;
  - displacing the needle guide along the first linear position sensing track;
  - determining that the hilt sensor has been activated;
  - measuring capacitance with the first plurality of active electrodes and the first plurality of passive electrodes.

11. The apparatus of claim 1, wherein the computer-readable storage medium further includes instructions that, when executed by the one or more processors, cause the apparatus to:
- determine if the needle length is within an allowed range; and
- if the needle is within the allowed range, display a third indication that the needle length is within the allowed range;
- if the needle is not within the allowed range, display a second indication that the needle length is not within the allowed range.

12. The apparatus of claim 1, wherein the finger receiver is a cylinder with a closed curved surface.

13. The apparatus of claim 1, wherein the finger receiver is a cylinder with an opened curved surface.

14. A method for inserting a needle into a patient, the method comprising:
- positioning, using a finger of a user, an apparatus for inserting a needle into a patient, the finger of the user inserted into a finger receiver on a base of the apparatus;
- prompting a user to measure a length of the needle;
- determining, using a first linear position sensing track and a needle holder, the length of the needle;
- prompting the user to set a target insertion depth for the needle;
- determining, using a second linear position sensing track and an insertion depth slider, the target insertion depth of the needle;
- determining, using an angle sensor, an insertion angle, wherein the insertion angle is an angle of a swing arm with respect to the base;
- prompting the user to insert the needle into the patient;
- based at least in part on the needle length and the insertion angle, determining that the user has inserted the needle to the target insertion depth; and
- providing a first indication to the user that the needle has been inserted to the target insertion depth.

15. The method of claim 14, further comprising:
- comparing the angle of the swing arm to a target angle; and
- providing a second indication to the user when the angle of the swing arm is within a threshold angle of the target angle.

16. The method of claim 15, wherein the threshold angle is about 1 degree.

17. The method of claim 14, further comprising:
- after prompting the user to set the needle length, displaying a current needle length on a display;
- after prompting the user to set the target insertion depth, displaying a current insertion depth on the display; and
- after prompting the user to set the insertion angle, displaying a current insertion angle on the display,
- wherein the current needle length changes as the user moves a needle guide along the first linear position sensing track,
- wherein the current insertion depth changes as the user moves the insertion depth slider along the second linear position sensing track, and
- wherein the current insertion angle changes as the user adjusts the angle of the swing arm.

18. The method of claim 14, wherein the first indication, a second indication and a third indication comprises any combination of one or more of illuminating an light-emitting diode, altering content of a display, and playing a sound.

19. The method of claim 14, wherein determining the length of the needle comprises determining that a hilt sensor has been activated.

20. The method of claim 14, further comprising:
- determining if the needle length is within an allowed range; and
- if the needle length is within the allowed range, displaying a second indication that the needle length is within the allowed range;
- if the needle is not within the allowed range, displaying a third indication that the needle length is not within the allowed range.

21. The method of claim 20, wherein the allowed range is 2 cm or more.

22. The method of claim 14, further comprising:
- determining if the needle insertion depth is within an allowed range; and
- if the needle insertion depth is within the allowed range, displaying a second indication that the needle insertion depth is within the allowed range;
- if the needle insertion depth is not within the allowed range, displaying a third indication that the needle insertion depth is not within the allowed range.

* * * * *